US006404911B2

(12) United States Patent
Ishihara et al.

(10) Patent No.: US 6,404,911 B2
(45) Date of Patent: Jun. 11, 2002

(54) SEMICONDUCTOR FAILURE ANALYSIS SYSTEM

(75) Inventors: Kazuko Ishihara, Fujisawa; Seiji Ishikawa, Kawasaki; Masao Sakata, Hiratsuka; Isao Miyazaki, Isesaki; Yoshiyuki Miyamoto, Takasaki; Jun Nakazato, Tokyo, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/731,745

(22) Filed: Dec. 8, 2000

Related U.S. Application Data

(63) Continuation of application No. 08/381,490, filed on Jan. 31, 1995, now Pat. No. 6,185,324, which is a continuation-in-part of application No. 07/908,550, filed on Jun. 30, 1992, now Pat. No. 5,841,893, which is a continuation of application No. 07/550,942, filed on Jul. 11, 1990, now abandoned.

(30) Foreign Application Priority Data

| Jul. 12, 1989 | (JP) | ............................................. 1-177934 |
| Jan. 31, 1994 | (JP) | ............................................. 6-009915 |
| Oct. 19, 1994 | (JP) | ............................................. 6-253772 |

(51) Int. Cl.$^7$ ................................................. G06K 9/00
(52) U.S. Cl. ..................... 382/149; 382/194; 382/203
(58) Field of Search ................................. 382/141, 144, 382/145, 149, 195, 201, 203, 286, 243, 194; 714/25, 737; 348/87, 125–126; 250/559.04, 559.05; 702/117; 438/16

(56) References Cited

U.S. PATENT DOCUMENTS

| 3,751,647 A | 8/1973 | Maeder et al. ......... 225/151.11 |
| 3,873,972 A | 3/1975 | Levine ....................... 382/243 |
| 4,189,711 A | 2/1980 | Frank ........................ 382/242 |
| 4,365,318 A | 12/1982 | Aichelman, Jr. et al. ... 382/243 |
| 4,449,818 A | * 5/1984 | Yamaguchi et al. ........ 356/237 |

(List continued on next page.)

FOREIGN PATENT DOCUMENTS

| JP | 5619635 | 2/1981 | .......... H01L/21/68 |
| JP | 58165337 | 9/1983 | .......... H01L/21/66 |

(List continued on next page.)

OTHER PUBLICATIONS

NEC Technical Report, vol. 46, No. 11, 1993 Memory Failure Analysis with An Exper System.
"IS–200 Patterned Wafer System Inspection System" by Hitachi, Ltd.
Przybyla et al., A Fully Integrated Photolithography Workcell, May 1989, 100–107, IEEE.
Henderson, "A Production Fab Defect Reduction Program", May 1989, 58–60, IEEE.

*Primary Examiner*—Timothy M. Johnson
(74) *Attorney, Agent, or Firm*—Antonelli, Terry, Stout & Kraus, LLP

(57) ABSTRACT

A semiconductor failure analysis system and method therefor facilitated by a failure information collection unit for collection, by bit, failure information of a semiconductor, an inspection unit for examining relations between various types of inspection data obtained by inspection of the semiconductor and for examining relations between the inspection data and failure information, a storage unit for storing design information of the semiconductor, an analysis unit for analyzing the failure information from the failure information collection unit, from the inspection unit and design information stored in the storage unit, a display unit for displaying at least one of the result of analysis from the analysis unit and the failure information, a failure cause estimation unit for estimating a cause of the failure information, and a unit for feeding the estimated cause of the failure information back to a process in which the failure has occurred.

16 Claims, 29 Drawing Sheets

U.S. PATENT DOCUMENTS

| | | | |
|---|---|---|---|
| 4,659,220 A | 4/1987 | Bronte et al. | 348/126 |
| 4,719,357 A | 1/1988 | Ayata et al. | 364/559 |
| 4,783,841 A | 11/1988 | Crayson | 382/243 |
| 4,817,184 A | 3/1989 | Thomason et al. | 382/8 |
| 4,851,902 A | 7/1989 | Tezuka et al. | 382/8 |
| 4,881,863 A | 11/1989 | Bragnisky | 382/8 |
| 4,894,790 A | 1/1990 | Yotsuya et al. | 382/8 |
| 4,908,871 A | 3/1990 | Hara et al. | 382/147 |
| 4,928,313 A | 5/1990 | Leonard et al. | 382/149 |
| 4,942,618 A | 7/1990 | Sumi et al. | 382/8 |
| 4,958,373 A | 9/1990 | Usami | 382/8 |
| 4,965,515 A | 10/1990 | Karasawa | 348/126 |
| 4,969,198 A | 11/1990 | Batchelder et al. | 382/147 |
| 5,070,532 A | 12/1991 | Faul et al. | 382/166 |
| 5,093,797 A | 3/1992 | Yotsuya et al. | 358/101 |
| 5,109,438 A | 4/1992 | Alves et al. | 382/243 |
| 5,153,444 A | 10/1992 | Maeda et al. | 250/559.45 |
| 5,216,726 A | 6/1993 | Heaton | 382/243 |
| 5,228,097 A | 7/1993 | Kumagal | 382/242 |
| 5,497,381 A * | 3/1996 | O'Donoghue et al. | 714/745 |
| 5,841,893 A | 11/1998 | Ishikawa et al. | 382/145 |

FOREIGN PATENT DOCUMENTS

| | | | |
|---|---|---|---|
| JP | 5967638 | 4/1984 | H01L/21/50 |
| JP | 59-228726 | 12/1984 | H01L/21/66 |
| JP | 60171736 | 9/1985 | H01L/21/66 |
| JP | A-61-243378 | 10/1986 | G01R/31/28 |
| JP | 63-135848 | 11/1986 | G01N/21/88 |
| JP | 6276712 | 4/1987 | H01L/21/02 |
| JP | A-62-169342 | 7/1987 | H01L/21/66 |
| JP | 62220839 | 9/1987 | G01N/21/88 |
| JP | 62276441 | 12/1987 | G01N/21/88 |
| JP | 6366446 | 3/1988 | G01N/21/88 |
| JP | 6366447 | 3/1988 | G01N/21/88 |
| JP | 63110744 | 5/1988 | H01L/21/66 |
| JP | 63220513 | 9/1988 | H01L/21/02 |
| JP | 6473241 | 3/1989 | G01N/21/88 |
| JP | 1-122132 | 5/1989 | H01L/21/66 |
| JP | 1-137641 | 5/1989 | H01L/21/66 |
| JP | 1-151243 | 6/1989 | H01L/21/66 |

* cited by examiner

FIG.18

| | NAME | FAULT DISTRIBUTION | CAUSE | NAME | FAULT DISTRIBUTION | CAUSE |
|---|---|---|---|---|---|---|
| BOTH-END CONNECTED | Y-STRIPE LINE | | FAIL OF DECODER | CONNECTED T-LINE | | FAIL OF DECODER |
| SINGLE CONNECTED | SINGLE CONNECTED STRIPE LINE | | PERIPHERAL CIRCUIT | SINGLE CONNECTED BLOCK | | PERIPHERAL CIRCUIT |
| NOT-CONNECTED | X-PERIODIC PAIR BIT | | FAIL OF POWER SOURCE CONTACT | SINGLE CROSS LINE | | SHORT AT INTERSECTING POINT |
| | PERIODIC | | | NON-PERIODIC | | |

| | KIND | FORMAT | COMPRESSING METHOD |
|---|---|---|---|
| ① | SINGLE POINT | A SINGLE FB IS SURROUNDED BY GOOD BITS | EXPRESSION OF DATA : (X,Y)<br>(X,Y) : BIT ADDRESS |
| ② | Y-PAIR BITS | TWO FAIL BITS ARE CONNECTED IN Y-DIRECTION | EXPRESSION OF DATA : (X,Y)<br>(X,Y) : HEAD BIT ADDRESS |
| ③ | X-PAIR BITS | TWO FAIL BITS ARE CONNECTED IN X-DIRECTION | EXPRESSION OF DATA : (X,Y)<br>(X,Y) : HEAD BIT ADDRESS |
| ④ | Y-LINE | N FAIL BITS ARE CONNECTED IN Y-DIRECTION (N>2) | EXPRESSION OF DATA : (X,Y,K)<br>(X,Y) : HEAD BIT ADDRESS<br>K : NUMBER OF CONTINUOUS BITS |
| ⑤ | X-LINE | N FAIL BITS ARE CONNECTED IN X-DIRECTION (N>2) | EXPRESSION OF DATA : (X,Y,K)<br>(X,Y) : HEAD BIT ADDRESS<br>K : NUMBER OF CONTINUOUS BITS |
| ⑥ | BLOCK | FAIL BITS ARE IN A STATE OF BLOCK | EXPRESSION OF DATA: (x1,y1,x2,y2)<br>(x1,y1):LEFT UPPER END BIT ADDRESS<br>(x2,y2):RIGHT LOWER END BIT ADDRESS |

SEMICONDUCTOR FAILURE ANALYSIS SYSTEM

CROSS-REFERENCE TO RELATED APPLICATIONS

This is a continuation of U.S. application Ser. No. 08/381,490 filed Jan. 31, 1995, now U.S. Pat. No. 6,185,324; which is a continuation-in-part of U.S. application Ser. No. 07/908,550 filed Jun. 30, 1992 entitled "INSPECTION DATA ANALYZING SYSTEM", and now U.S. Pat. No. 5,841,893, which is a continuation of Ser. No. 07/550,942 filed Jul. 11, 1990, now abandoned; and the entire disclosures of which are incorporated herein by reference.

BACKGROUND OF THE INVENTION

The present invention relates to a semiconductor failure analysis system and a semiconductor checking apparatus and particularly, relates to a semiconductor failure analyzing system adapted for analysis the cause of a failure in a semiconductor wafer production and a semiconductor checking apparatus used in the failure analysis system.

According to one to conventional semiconductor failure analysis system, namely, JP-A-61-243378 a failure analysis system is provided in which: distribution patterns of points obtained by an electrical test and an indication of whether the quality of a subject under inspection is good or bad are classified into basic patterns so that the basic patterns are stored in a storage device; information indicating a plurality of possibilities that a failure has occurred in the subject under inspection is generated correspondingly to basic patterns obtained from basic failure information which can be considered with respect to the all basic patterns stored in the storage device; and the coordinates of points at which the occurrence of the failure is estimated are automatically transferred to an observation apparatus.

In the conventional system, there is however no consideration that means for observing information concerned with results of failure analysis systematically from a large number of viewpoints is provided in an user interface of the system. That is, there is no consideration that information concerned with results of failure analysis, such as display indicating fail bits on the whole of a wafer, display indicating the distribution of fail bits on an arbitrary chip, enlarged display indicating the distribution of fail bits in a partial area of a chip, and so on, is used speedily and smoothly. Whether the aforementioned information is to be displayed or not to be displayed, it is necessary to operate a display unit to switch the scene on the display unit to a new scene. Accordingly, operations which can be very troublesome for users are often required.

Further, in the conventional system, there has been proposed no method in which the sizes of memory cells can be confirmed visually with respect to the user interface of the system when information is displayed.

Further, in the conventional semiconductor failure analysis system, no consideration is given that errors may occur when the coordinates of points at which the occurrence of the failure is estimated are transferred to the observation apparatus because different coordinate reference points are used. Further, patterns of generation of fail bits are classified, but there is no specific rule for the classification. In the conventional system, therefore, all causes of failure distributions are estimated so that a small number of basic patterns thus classified have one-to-one correspondence with the causes of the failure. In the conventional system, however no consideration is given that a plurality of causes of the failure correspond to one and the same pattern of fail bits, though such correspondence must be thought of. Further, because the causes related to the basic patterns are difficult to determine, a large time is required for examining the true cause of the failure. Further, because there is no consideration that the relation between the pattern of generation of fail bits and the cause of the failure varies in accordance with the subject under inspection, the conventional system cannot be adapted to multikind subjects of inspection.

Further, because there has not been proposed a function of managing the situation of occurrence of fail bits statistically on the basis of the classified basic patterns to thereby feed results of the management back to a production process, the conventional system has a risk that the occurrence of a failure may be detected later when the failure has occurred in the production process.

In addition, though a micro analyzing method in which the situation of occurrence of fail bits in a wafer or in a chip is analyzed bit by bit is employed in the conventional system, there has not been proposed a macro analyzing method in which the patterns of generation of fail bits are categorized so that macro analysis is performed by using the category thereof.

SUMMARY OF THE INVENTION

The present invention is designed to solve the aforementioned problems in the prior art.

A first object of the present invention is to provide a semiconductor failure analysis system in which the cause of a failure is examined easily, accurately and speedily with the advance of integration of semiconductor memory when fail bits are subjected to failure analysis.

A second object of the present invention is to provide a semiconductor failure analysis system in which unification of coordinate systems varying in accordance with respective inspection apparatuses and correction of measurement errors dependent on the respective apparatuses can be performed so that failure analysis can be carried out accurately and speedily by using a plurality of inspection data with the advance of integration of the semiconductor memory.

A third object of the present invention is to provide a semiconductor checking apparatus in which measurement errors can be corrected for the failure analysis of a semiconductor.

The above first object of the present invention is achieved by a semiconductor failure analysis system which includes a failure information collection unit for collecting, by bit, failure information concerned with a failure of a semiconductor, an inspection unit for inspecting the failure information concerned with the failure of the semiconductor, a storage unit for storing information concerned with the design of the semiconductor, an analysis unit for analyzing the failure information on the basis of output information outputted from the failure information collection unit, output information outputted from the inspection unit and design information stored in the storage unit, a display unit for displaying at least one of the result of analysis of the analysis unit and the failure information, a failure cause estimation unit for estimating the cause of the failure information, and a feeding unit for feeding the estimated cause of the failure back to a process in which the failure has occurred.

The above second object of the present invention is achieved by a semiconductor failure analysis system which includes a failure information collection unit for collecting, by bit, failure information concerned with a failure of a semiconductor, an inspection unit for inspecting the failure information of the semiconductor by using a plurality of inspection apparatuses, an analysis unit for analyzing the failure information on the basis of output information outputted from the failure information collection unit and output information outputted from the inspection unit, a display unit for displaying at least one of the result of analysis of the analysis unit and the failure information, and a correction unit for correcting measurement errors between the plurality of inspection apparatuses.

The above third object of the present invention is achieved by a semiconductor checking apparatus which includes a failure information collection unit for collecting, by bit, failure information concerned with a failure of a semiconductor, an inspection unit for inspecting the failure information of the semiconductor, a display unit for displaying at least one of output information outputted from the inspection unit and the failure information, and a correction unit for correcting measurement errors in the inspection unit.

In the present invention, failure information is analyzed on the basis of information outputted from the failure information collection unit, information outputted from the inspection unit and design information stored in the storage means. Accordingly, the failure information can be analyzed by referring to information concerned with the arrangement of memory cells correspondingly to the kind of each chip, so that a coordinate system can be set on the basis of one chip. Further, in the present invention, the cause of semiconductor failure information collected by the failure information collection unit is estimated by the failure cause estimation unit so that a result of the estimation is fed back to a process in which the failure has occurred. Accordingly, measures can be taken speedily against abnormality in the production process.

Further, in the present invention, there is provided a correction unit for correcting measurement errors between a plurality of inspection apparatuses. Accordingly, relative correction values can be calculated even in the case where measurement errors are present between respective apparatuses. Further, in the present invention, the failure information is classified in relation to the cause of the failure so that a result of the classification is analyzed. Accordingly, any person which is not a specialist may perform failure analysis.

Further, inspection apparatuses used in the present invention are those which can be used in the aforementioned semiconductor failure analysis system. Accordingly, relative correction values can be calculated by the correction means even in the case where measurement errors are present between the inspection apparatuses.

BRIEF DESCRIPTION OF THE DRAWINGS

FIG. 18 is an explanatory view showing relations between patterns of generation of fail bits and causes of failures.

FIG. 27 is an explanatory view showing a table of relations between category patterns and causes of failures as displayed in the display unit.

FIG. 32 is an explanatory view showing classification of fail bit formats and compression methods.

DESCRIPTION OR THE PREFERRED EMBODIMENTS

Referring now to the block diagram shown in FIG. 1, the basic concept of a failure analysis system according to the present invention will be described.

Figure 1:
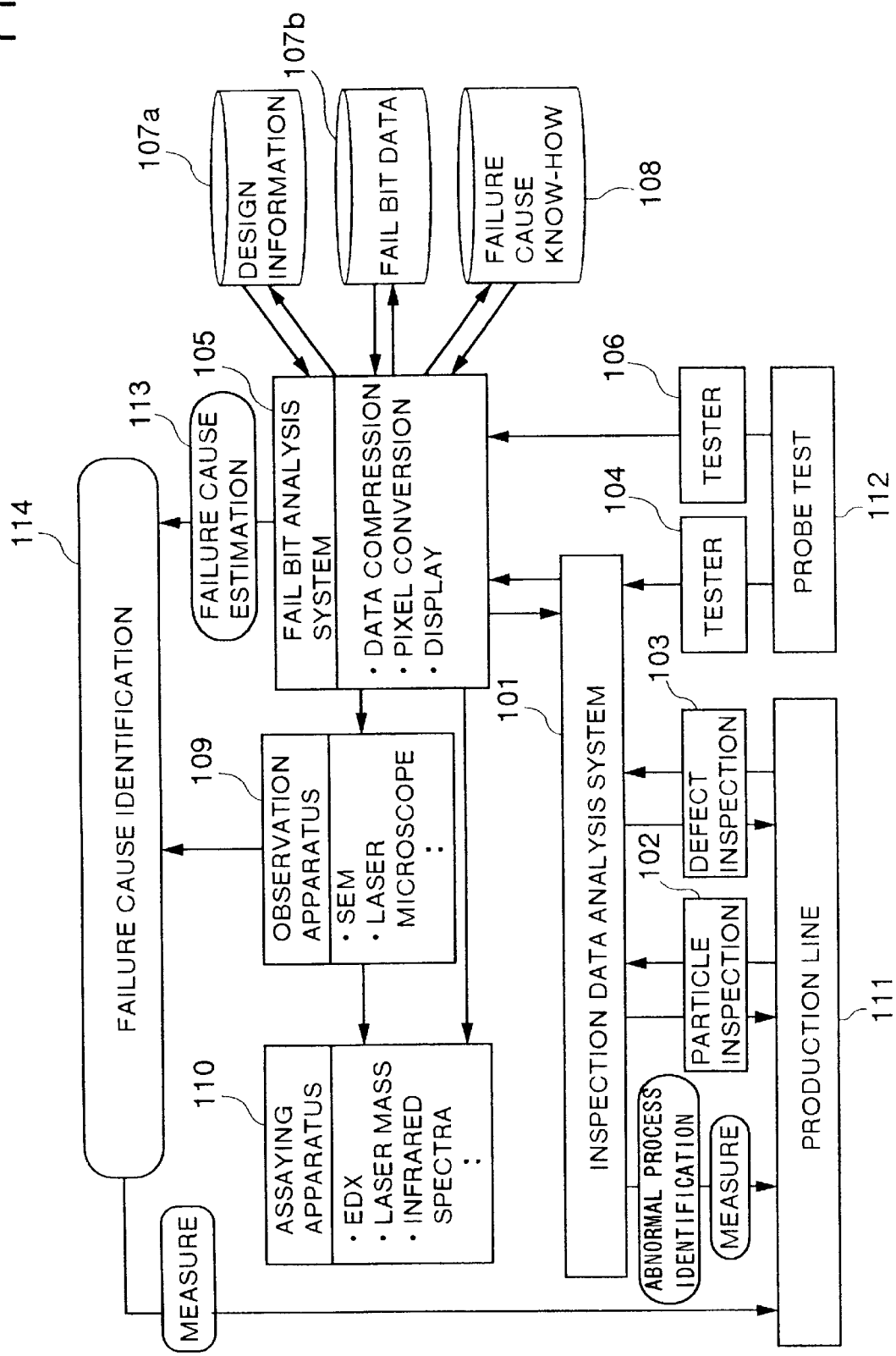
FIG. 1 is a block diagram showing the basic concept of a failure analysis system according to the present invention.

In FIG. 1, an inspection data analysis system 101 performs analysis on the basis of data obtained from particle inspection 102 and defect inspection 103 in a production line 111, data obtained from a tester 1 (104) in a wafer final test or probe test 112 and data obtained from a fail bit analysis system (FB analysis system) 105 in the probe test 112.

The FB analysis system 105 extracts a failure point and a failure induction point from the distribution pattern of failure bits by using LSI design information and failure bit data obtained from a tester 2 (106) in the probe test 112 and performs estimation 113 of the cause of a failure by referring to failure cause know-how information. Therefore, a design information data base 107a for storing LSI design information, a fail bit data base 107b for storing fail bit data and a failure cause know-how data base 108 for storing failure cause know-how information are connected to the FB analysis system 105. Further, an observation apparatus 109 observes the coordinates of the failure point and the failure induction point given by the FB analysis system 105 and specifies the cause and process of the failure as represented by the reference numeral 114. An analyzing apparatus 110 performs component analysis of foreign matter or the like detected by the observation apparatus 109 and specifies the cause and process of the failure.

Figure 2:
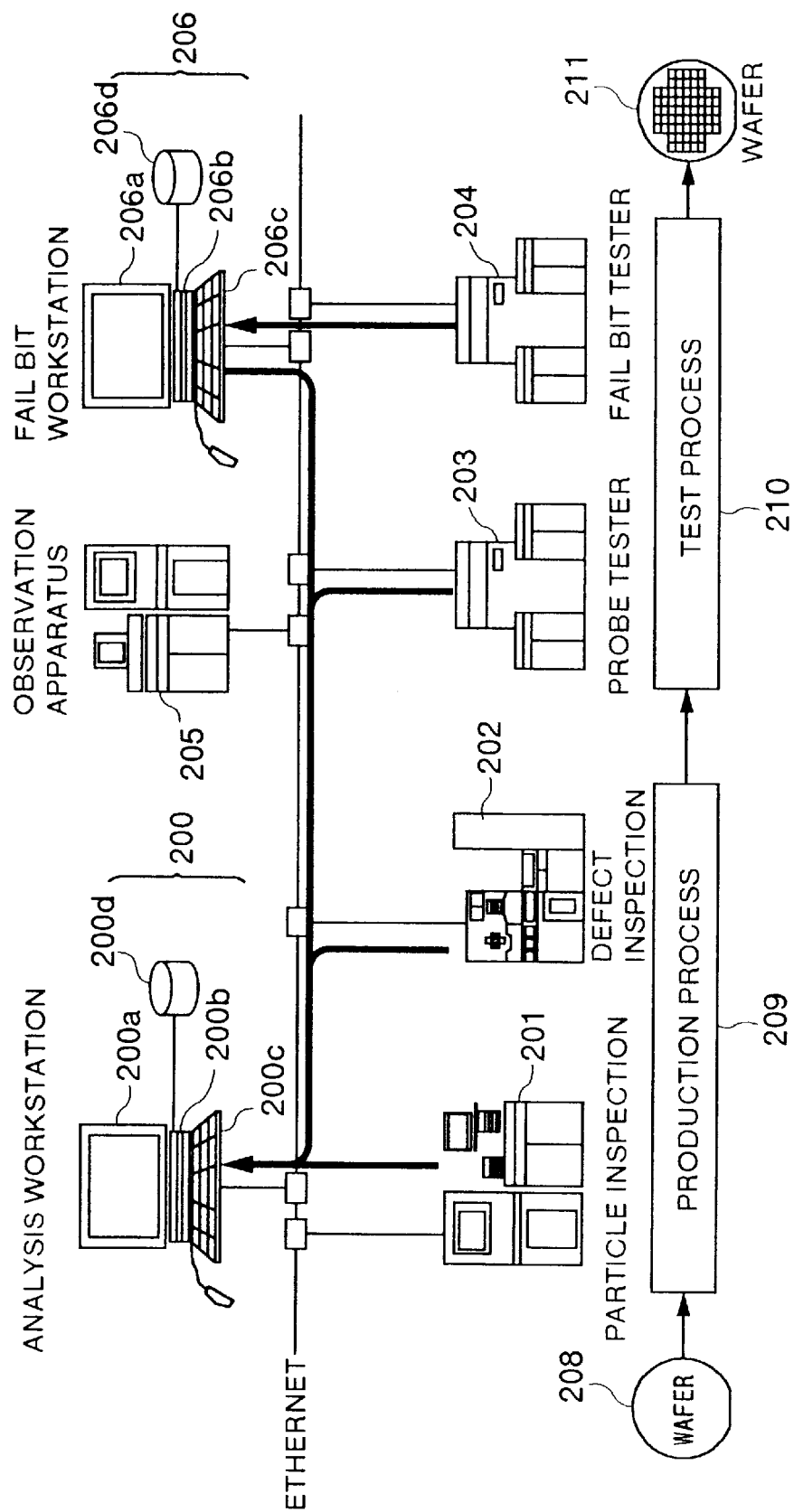
FIG. 2 is a hardware block diagram showing an embodiment of the failure analysis system according to the present invention.

FIG. 2 is a hardware block diagram showing an embodiment of the semiconductor failure analysis system according to the present invention. As shown in FIG. 2, the semiconductor failure analysis system in this embodiment comprises an analysis workstation (analysis WS) 200 constituting the aforementioned inspection data analysis system 101 for analyzing inspection data, a particle inspection apparatus 201 for performing the aforementioned particle inspection 102, a defect inspection apparatus 202 for performing the aforementioned defect inspection 103, inspection apparatuses such as a probe tester 203, a fail bit tester 204, and so on, an observation apparatus 205 equivalent to the observation apparatus 109, and a fail bit workstation (fail bit WS) 206 constituting the FB analysis system 105 for performing estimation of the cause of the failure, or the like.

The analysis WS 200 includes a display unit 200a for performing display, a processor 200b at least having a central processing unit (CPU) for performing various types of processing such as processing of an arithmetic operation, or the like, a main storage and an internal auxiliary storage, an input unit 200c such as a mouse and a keyboard for performing various types of input operations, and an external hard disk 200d. Like the analysis WS 200, the fail bit WS 206 includes a display unit 206a for performing display, a processor 206b at least having a central processing unit (CPU) for performing various types of processing such as processing of an arithmetic operation, a main storage and an internal auxiliary storage, an input unit 206c such as a mouse and a keyboard for performing various types of input operations, and an external hard disk 206d.

After chips are formed on a wafer 208 in a production process 209 and then the wafer 208 is tested by the failure analysis system of this embodiment or the like in a test process 210, only the wafer 208 is shipped as a wafer 211 on which good chips are produced.

Figure 11:
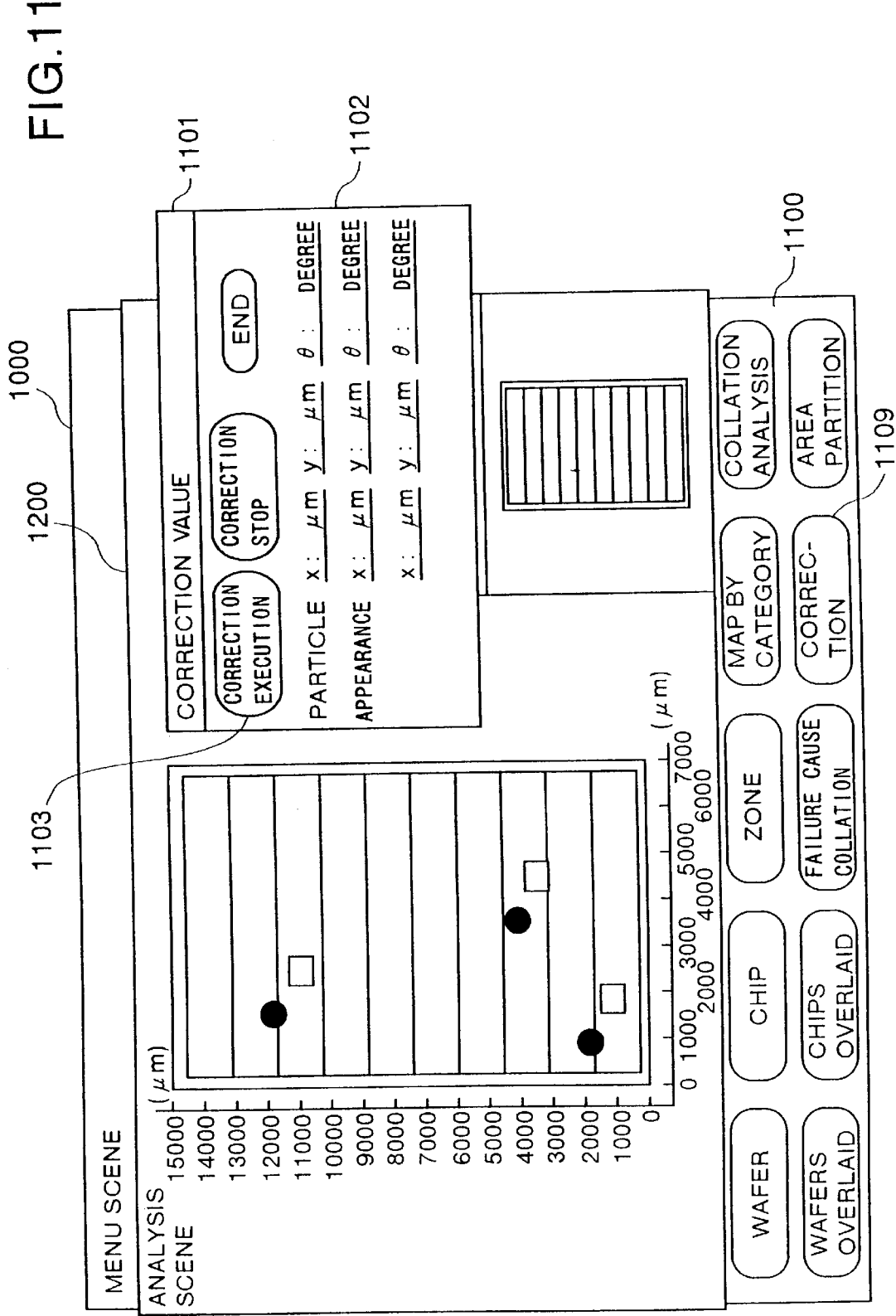
FIG. 11 is an explanatory view showing an input scene which is displayed on a display unit for correcting measurement errors in inspection apparatuses.
Figure 12:
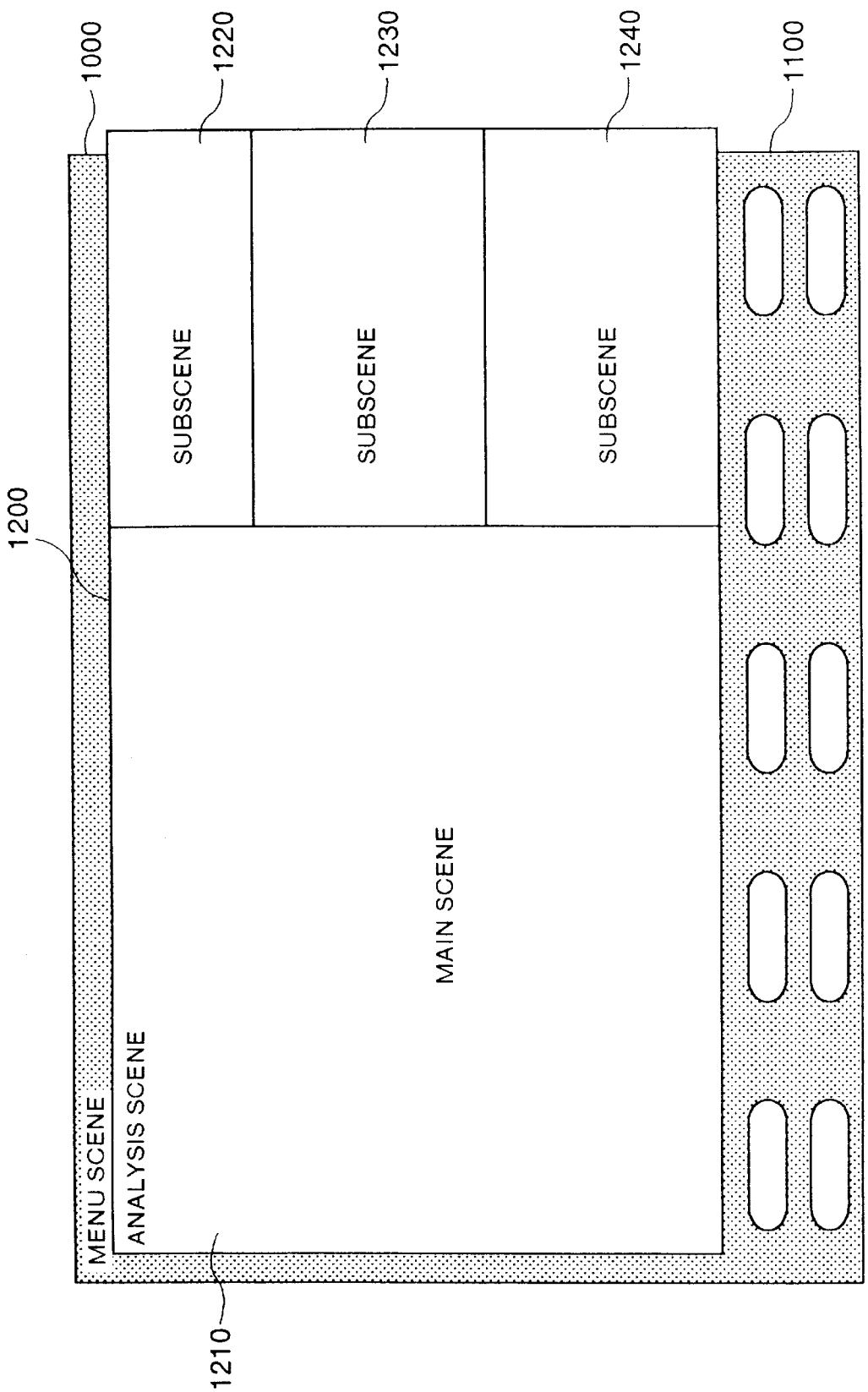
FIG. 12 is an explanatory view showing the structure of a system scene displayed on the display unit.

In the display unit 200a (or 206a), a scene for performing various displays and indications is displayed. As shown in FIGS. 11 and 12, a multi-window system is substantially employed. That is, a menu scene 1000 is first displayed. Items selected to be inputted are displayed at the lower portion of the menu scene 1000. In this embodiment, selection items "wafer", "chip", "zoom", "category map", "check analysis", "wafers overlaid", "chips overlaid", "collation of the cause of failure", "correction" and "area partition" are displayed. In the embodiment shown in FIG. 11, a correction value input scene 1101 is displayed by selecting the "correction" 1109 in the condition in which an analysis scene 1200 is displayed.

As the internal storage contained in the processor 200b (or 206b), for example, a hard disk HD can be used. As the external hard disk 200d (or 206d), a hard disk HD can be also used. Incidentally, optical disk devices or the like can be used.

As shown in FIG. 12, the analysis scene is separated into a main scene 1210 and subsidiary scenes 1220, 1230 and 1240.

Figure 3:
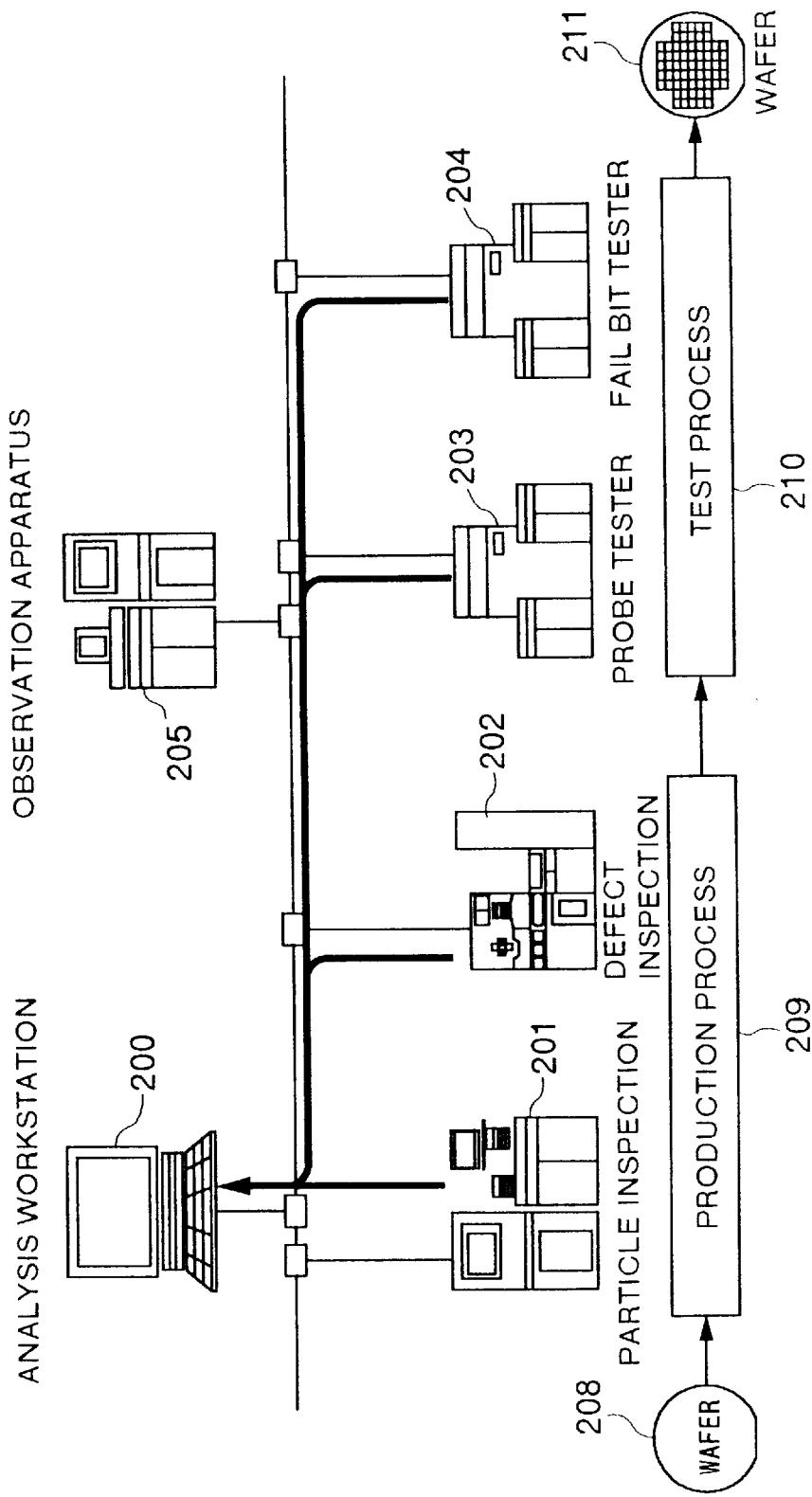
FIG. 3 is a hardware block diagram showing another embodiment of the failure analysis system according to the present invention.

Alternatively, the function of the fail bit WS 206 may be given to the analysis WS 200 so that the fail bit WS 206 can be omitted as shown in FIG. 3.

Figure 4:
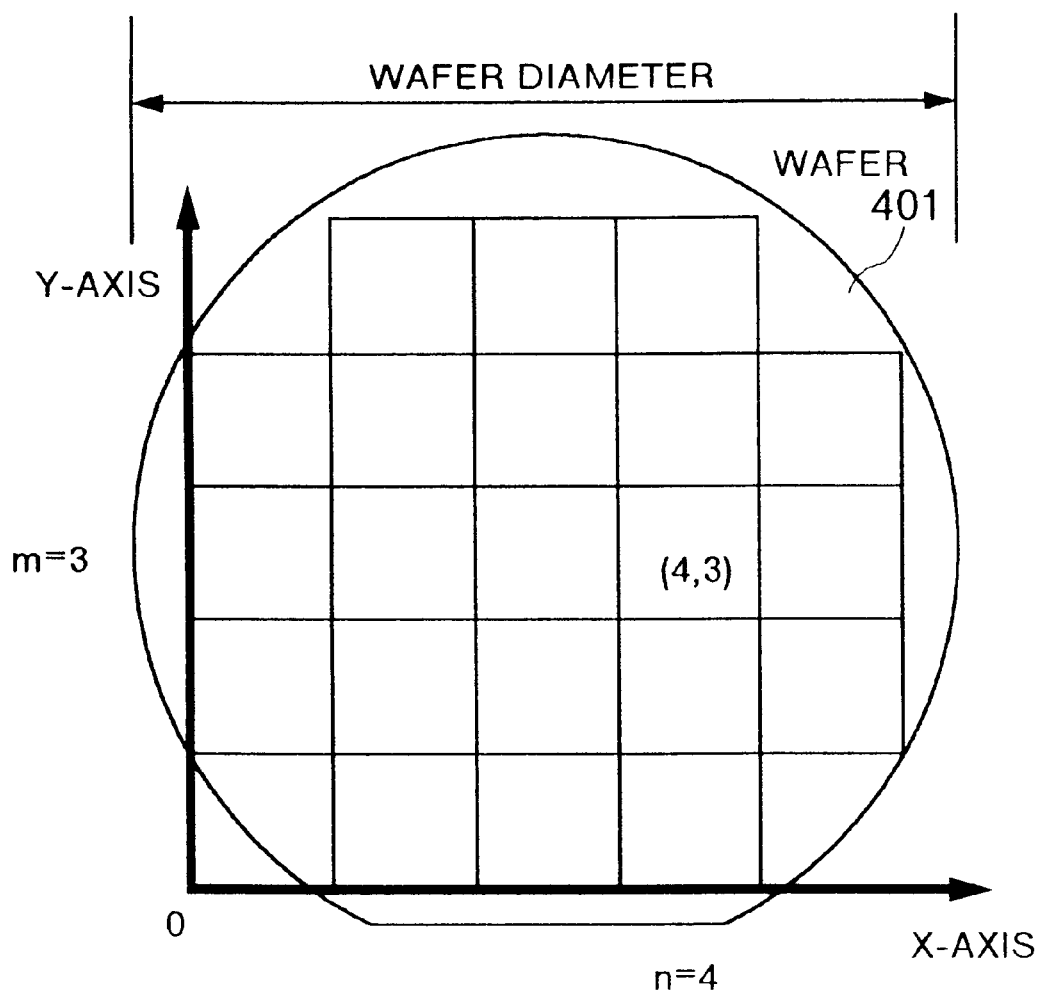
FIG. 4 is an explanatory view showing the outline of chips arranged on a wafer.
Figure 5:
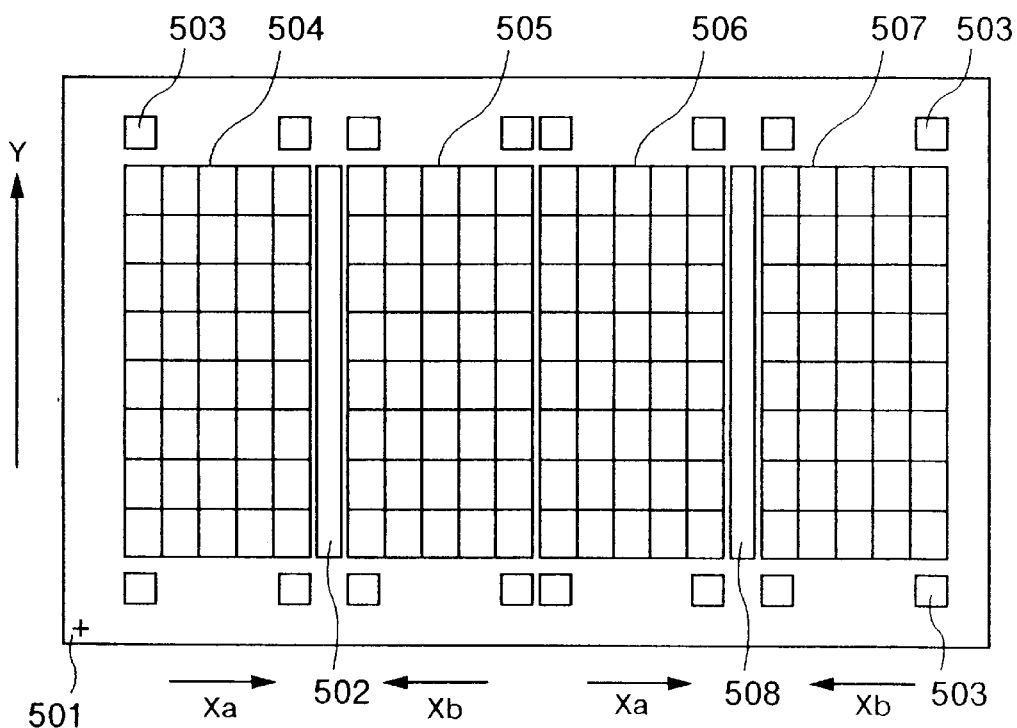
FIG. 5 is an explanatory view showing the internal structure of a chip.

Referring now to FIGS. 4 and 5, the situation of chips on a semiconductor wafer (hereinafter merely referred to as "wafer") and the internal structure of the chips will be described below. FIG. 4 is a view showing the situation of chips arranged on a wafer. As shown in FIG. 4, chips are arranged lengthwise and broadwise on a wafer 401 which is a subject of inspection. Thus, the chips are shaped like an oblong plate. As shown in FIG. 4, the position of a certain chip in the wafer 401 can be expressed in coordinates, for example, (4, 3).

FIG. 5 is a view showing the internal structure of the chips. A mark 501 indicating the origin in a chip is formed at an end of the chip. A plurality of external terminals (bonding pads) 503 are arranged in the periphery of the chip. For example, a memory mat (504–507) having a large capacity of 4 mega-bits is arranged in the center portion of the chip. This memory mat is divided into four parts, namely, a first memory mat 504, a second memory mat 505, a third memory mat 506 and a fourth memory mat 507. This memory mat is formed so that each of the memory mats 504 to 507 obtained by dividing this memory mat into four parts has a capacity of 1 mega-bits.

A peripheral circuit 502 containing a decoder circuit is arranged between the first and second memory mats 504 and 505. Similarly, a peripheral circuit 508 is arranged between the third and fourth memory mats 506 and 507. Further, in the first memory mat 504, memory cells (hereinafter merely referred to as "cell") are arranged in the form of meshes as shown in FIG. 5. In a group of cells in the second memory mat 505, a coordinate system is constituted by the mirror inversion pattern of the first memory mat 504. A group of cells in the third memory mat 506 are successively arranged in the same manner as in the first memory mat 504. A group of cells in the fourth memory mat 507 are successively arranged in the same manner as in the second memory mat 505.

LSI design information stored in the LSI design information data base 107a will be described now. LSI design information contains information concerned with the positions of arrangement of the aforementioned memory mats and the sizes of the memory mats, information concerned with wafer size, chip size and cell size, information concerned with the arrangement of chips in the wafer, the number of memory mats in a chip, the number of memory cells in a memory mat and the coordinates of the position of a coordinate reference pattern for determining the coordinates of a certain point in a chip, and information required for performing failure analysis of a plurality of semiconductors. The FB analysis system 105 in FIG. 1 analyzes fail bits (FB) at any time by referring to the LSI design information.

Figure 6:
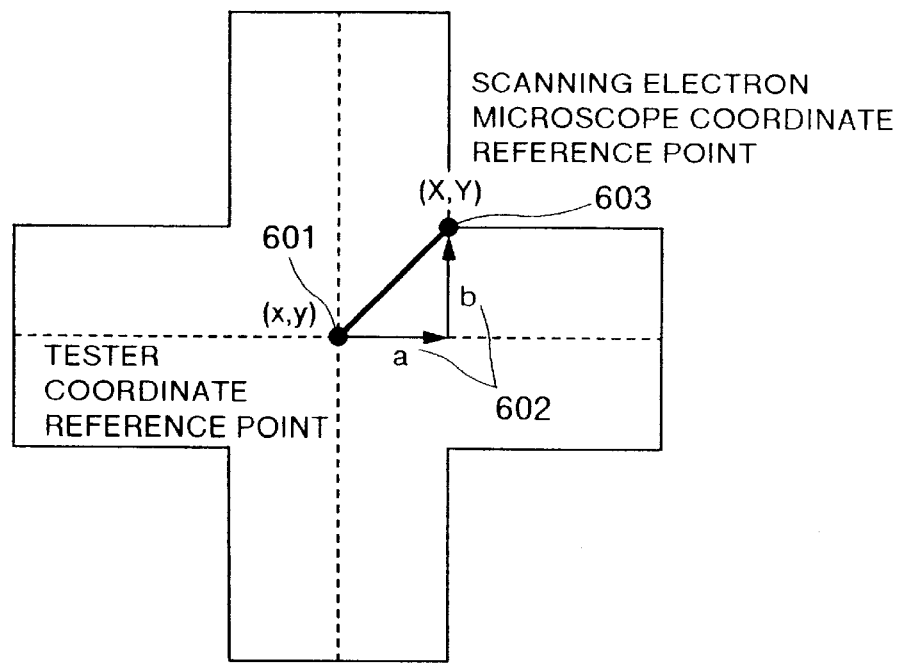
FIG. 6 is an explanatory view showing coordinate reference points in a chip.

Unification of coordinate systems among the respective inspection apparatuses or observation apparatuses will be described below. FIG. 6 shows a coordinate reference pattern in a chip. As the coordinate reference pattern, a coordinate reference pattern 501 in a chip as shown in FIG. 5 may be used. How to set a reference point in this pattern varies according to the inspection apparatuses or observation apparatuses. Therefore, the coordinates of the coordinate reference point for each inspection apparatus or observation apparatus and relative errors with respect to the inspection apparatus or observation apparatus are calculated on the basis of the design information in advance, so that the information concerned with the coordinates of the reference point and relative errors is registered in the LSI design information data base 107a. When data are to be transferred or when different inspection data are to be analyzed by comparison, the coordinates of a certain point are calculated by correcting the errors between the coordinate systems.

When, for example, an analyzing person is to transfer the coordinates of a certain memory cell after the analysis in the FB analysis system 105 in order to observe the memory cell under a scanning electron microscope (SEM) which is an observation apparatus 109 (205), the analyzing person must carry out the following process on a computer before data are transferred.

First, fail bit data (FB data) is transformed from the logical coordinates to the real coordinates. Further, the relative error between the coordinate systems of the SEM and the tester is corrected. That is, the coordinates (X, Y) of the FB data in the SEM coordinate system as designated by the reference numeral 603 are given by the following equation when the real coordinates of the FB data in the tester and correction values are (x, y) and (a, b) as designated by the reference numerals 601 and 602, respectively, as shown in FIG. 6.

(X, Y)=(x, y)+(a, b)

Accordingly, values of (x+a, y+b) are transferred. When the aforementioned data are to be collated with other data, the coordinates of the FB data can be transformed in the same manner as described above. Because this transformation allows the respective apparatuses to use data in the same coordinate system, work such as coordinate comparison, etc. between different apparatuses is simplified.

An automatic correcting function will be described below. Because coordinates systems must be unified between apparatuses when coordinates are compared between different inspection data such as fail bit data, defect inspection data, particle inspection data, and so on, errors may occur though the aforementioned coordinate transformation is performed. This is because measurement error may occur in each apparatus. Therefore, the following operation is carried out in order to correct these errors.

When, for example, coordinates are to be compared between particle inspection data and defect inspection data, particles which can detected by the particle inspection apparatus and the defect inspection apparatus are deposited on an experimental wafer in advance so that the wafer is measured by the particle inspection apparatus and the defect inspection apparatus to compare the measured coordinates of the particles deposited on the wafer. Correction values (x, y, θ) are calculated on the basis of results of the comparison, so that the calculated correction values (x,y, θ) are registered in the aforementioned LSI design information data base 107a. In the correction values (x, y, θ), x represents a correction value in the x direction, y represents a correction value in the y direction, and θ represents a correction value in the rotating direction.

The method of calculating the correction values is classified into a first method and a second method. In the first method, correction in the rotating direction is performed before correction in the x and y directions is performed. In the second method, correction in the rotating direction is performed after correction in the x and y directions is performed. In the first method, correction is carried out in accordance with the following expressions.

$$a = \frac{1}{n}\left\{\sum_{i=1}^{n}(Xi - \Delta x) - \sum_{i=1}^{n}(xi - \Delta x) + \theta\sum_{i=1}^{n}(yi - \Delta y)\right\} \quad (1)$$

$$b = \frac{1}{n}\left\{\sum_{i=1}^{n}(Yi - \Delta y) - \theta\sum_{i=1}^{n}(xi - \Delta x) - \sum_{i=1}^{n}(yi - \Delta y)\right\} \quad (2)$$

$$\theta = \frac{-\sum_{i=1}^{n}\{(Xi - \Delta x)(yi - \Delta y) - (xi - \Delta x)(Yi - \Delta y)\} - \frac{1}{n}\left\{\sum_{i=1}^{n}(xi - \Delta x)\sum_{i=1}^{n}(Yi - \Delta y) + \sum_{i=1}^{n}(xi - \Delta x)\sum_{i=1}^{n}(yi - \Delta y)\right\}}{\sum_{i=1}^{n}\{(Xi - \Delta x)(xi - \Delta x) + (yi - \Delta y)(Yi - \Delta y)\} - \frac{1}{n}\left\{\sum_{i=1}^{n}(xi - \Delta x)\sum_{i=1}^{n}(Xi - \Delta x) + \sum_{i=1}^{n}(yi - \Delta y)\sum_{i=1}^{n}(Yi - \Delta y)\right\}} \quad (3)$$

In the second method, correction is carried out in accordance with the following expressions.

$$a = \frac{1}{n}\left\{\sum_{i=1}^{n}(xi-\Delta x) - \sum_{i=1}^{n}(xi-\Delta x) - \theta\sum_{i=1}^{n}(Yi-\Delta y)\right\} \quad (4)$$

$$b = \frac{1}{n}\left\{\theta\sum_{i=1}^{n}(Xi-\Delta x) - \sum_{i=1}^{n}(Yi-\Delta y) + \sum_{i=1}^{n}(yi-\Delta y)\right\} \quad (5)$$

$$\theta = \frac{-\sum_{i=1}^{n}\{(Xi-\Delta x)(yi-\Delta y)-(xi-\Delta x)(Yi-\Delta y)\} - \frac{1}{n}\left\{\sum_{i=1}^{n}(xi-\Delta x)\sum_{i=1}^{n}(Yi-\Delta y) - \sum_{i=1}^{n}(xi-\Delta x)\sum_{i=1}^{n}(yi-\Delta y)\right\}}{\sum_{i=1}^{n}\{(Xi-\Delta x)(xi-\Delta x)+(yi-\Delta y)(Yi-\Delta y)\} - \frac{1}{n}\left\{\sum_{i=1}^{n}(xi-\Delta x)\sum_{i=1}^{n}(Xi-\Delta x) + \sum_{i=1}^{n}(yi-\Delta y)\sum_{i=1}^{n}(Yi-\Delta)\right\}} \quad (6)$$

In the expressions (1) to (6), (Xi, Yi) represent the coordinates of respective particles measured by the defect inspection apparatus 202, (xi, yi) represent the coordinates of respective particles measured by the particle inspection apparatus 201, ($\Delta x$, $\Delta y$) represent the coordinates of the center of rotation, and n represents the number of particles deposited on the wafer.

Because the correction values thus obtained are provided as relative correction values between the defect inspection apparatus 202 and the particle inspection apparatus 201, coordinates in one apparatus can be compared with coordinates in another apparatus as long as correction values can be calculated in the same manner as described above. In the expressions (1) to (6), $\theta$ is approximated by $\sin \theta = \theta$ and $\cos \theta = 1$ when $\theta$ is considered to be sufficiently near zero. As described above, in this embodiment, unification of coordinates between apparatuses and correction of errors measured correspondingly to the apparatuses are carried out, so that not only analysis is performed with high accuracy but also reduction of analyzing time is attained.

After inspection data are displayed in an analysis scene 1200 of the FB analysis system 105 or inspection data analysis system 101 as shown in FIG. 11, a human operator may confirm difference between coordinates and set correction values to perform manual correction. In this case, for example, the correction values are set by the following method. After inspection data are displayed on the screen of the inspection apparatus, "correction" 1109 is pointed by a mouse, or the like, in the input unit 200c (see FIG. 2). As a result, a correction value input scene 1101 as shown in FIG. 11 is displayed. The human operator inputs values for respective items.

As the correction value input method, there are two methods, for example, in the case of comparison between particle inspection data and defect inspection data. One is a method in which the coordinates of particle inspection data are made to approach the coordinates of defect inspection data. The other is a method in which the coordinates of defect inspection data are made to approach the coordinates of particle inspection data. In the former method, correction values are inputted to a correction value input line 1102 of particle inspection data but no values are inputted to a correction value input line of defect inspection data. In the latter method, correction values are inputted to the correction value input line of defect inspection data. When "execution of correction" 1103 is pointed by a mouse after the inputting of correction values, correction is executed. Transformation of coordinates in the inside of the computer is performed in the same manner as in the case of the automatic correcting function.

Referring to FIGS. 7 through 10, data processing algorithm in the FB analysis system will be described below.

Figure 7:
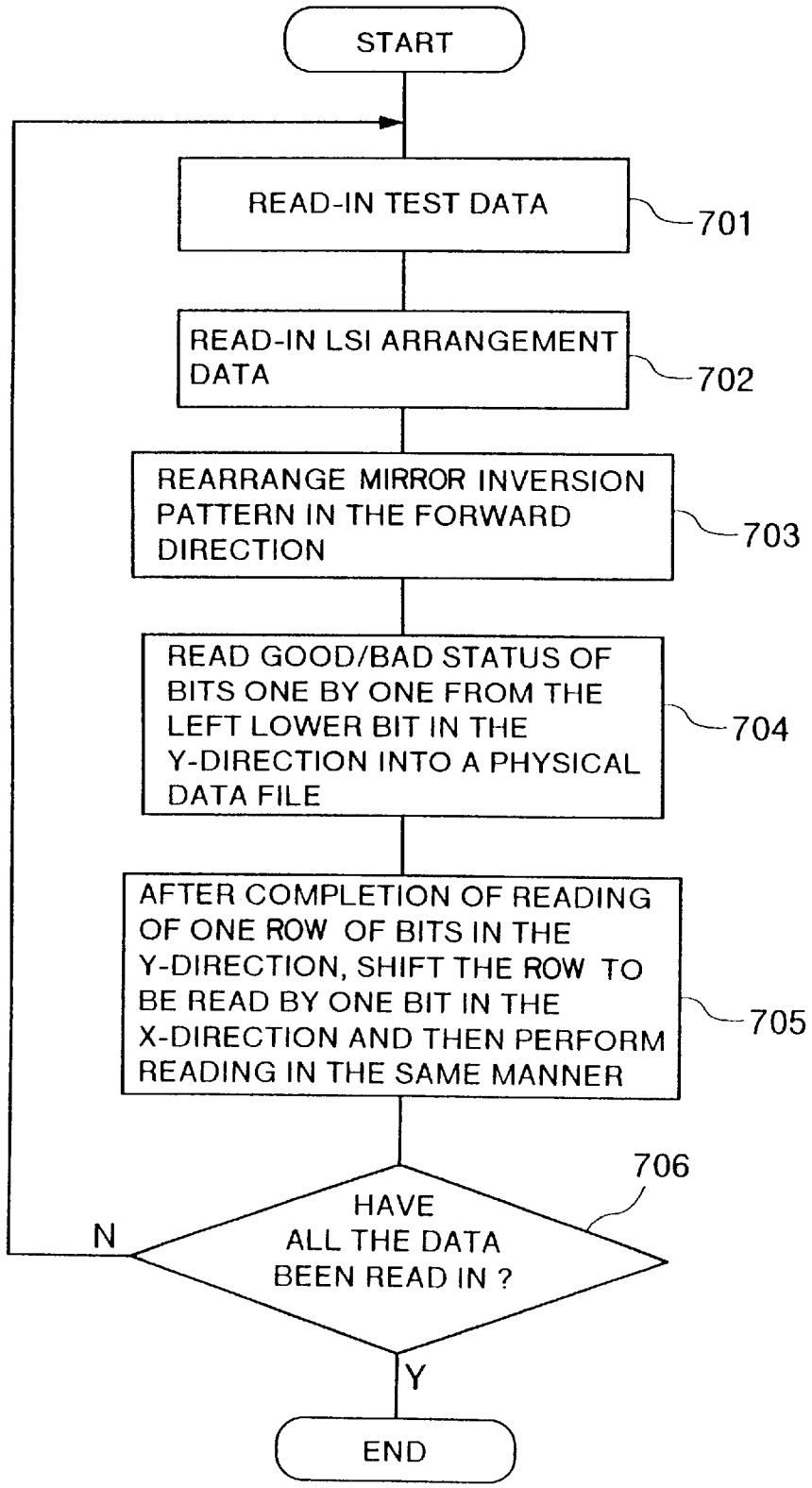
FIG. 7 is a flow chart for explaining the outline of physical transformation in the present invention.

FIG. 7 is a flow chart showing the outline of physical transformation. Physical transformation means replacement of logical coordinate system information in FIG. 5 by information in which memory cells are arranged linearly.

First, test data are read from the FB data base 107b (step 701) and LSI arrangement data are read from the LSI design information data base 107a (step 702). Then, memory cell design information formed in the aforementioned mirror inversion pattern is rear-ranged in the forward direction (step 703). Then, good/bad states (quality) of bits are read one by one into a physical data file in the Y direction so that the reading is started from the left lower bit in FIG. 5 (step 704).

When the reading of one row of bits in the Y direction is completed, the point to read bits is shifted by one bit in the X direction and then quality of bits are recorded one by one in the Y direction in the same manner as described above (step 705). Unless all data are read, the aforementioned procedure is repeated (step 706).

Figure 8:
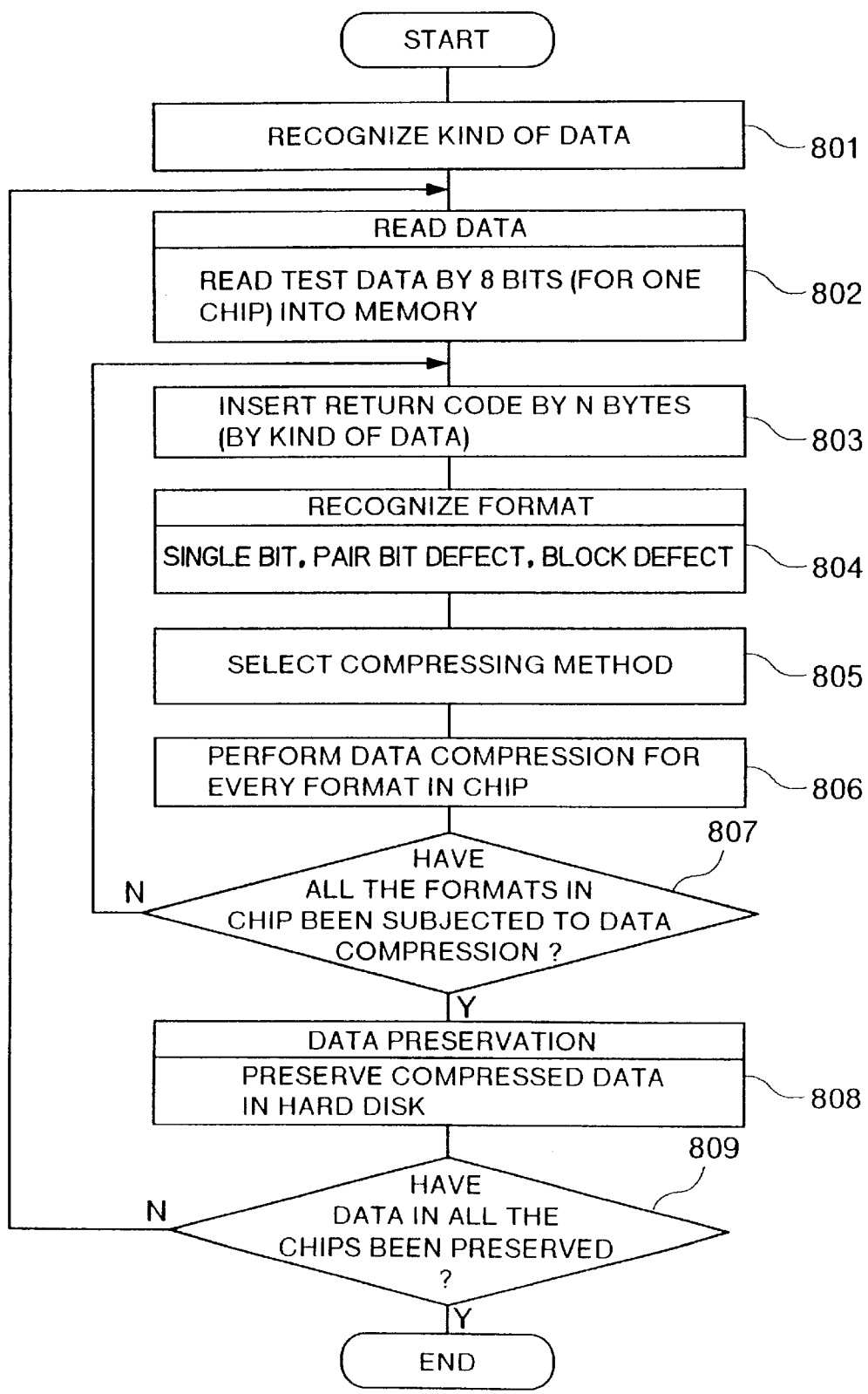
FIG. 8 is a flow chart of a routine for using several compression methods each in accordance with the fail bit format in a chip.
Figure 9:
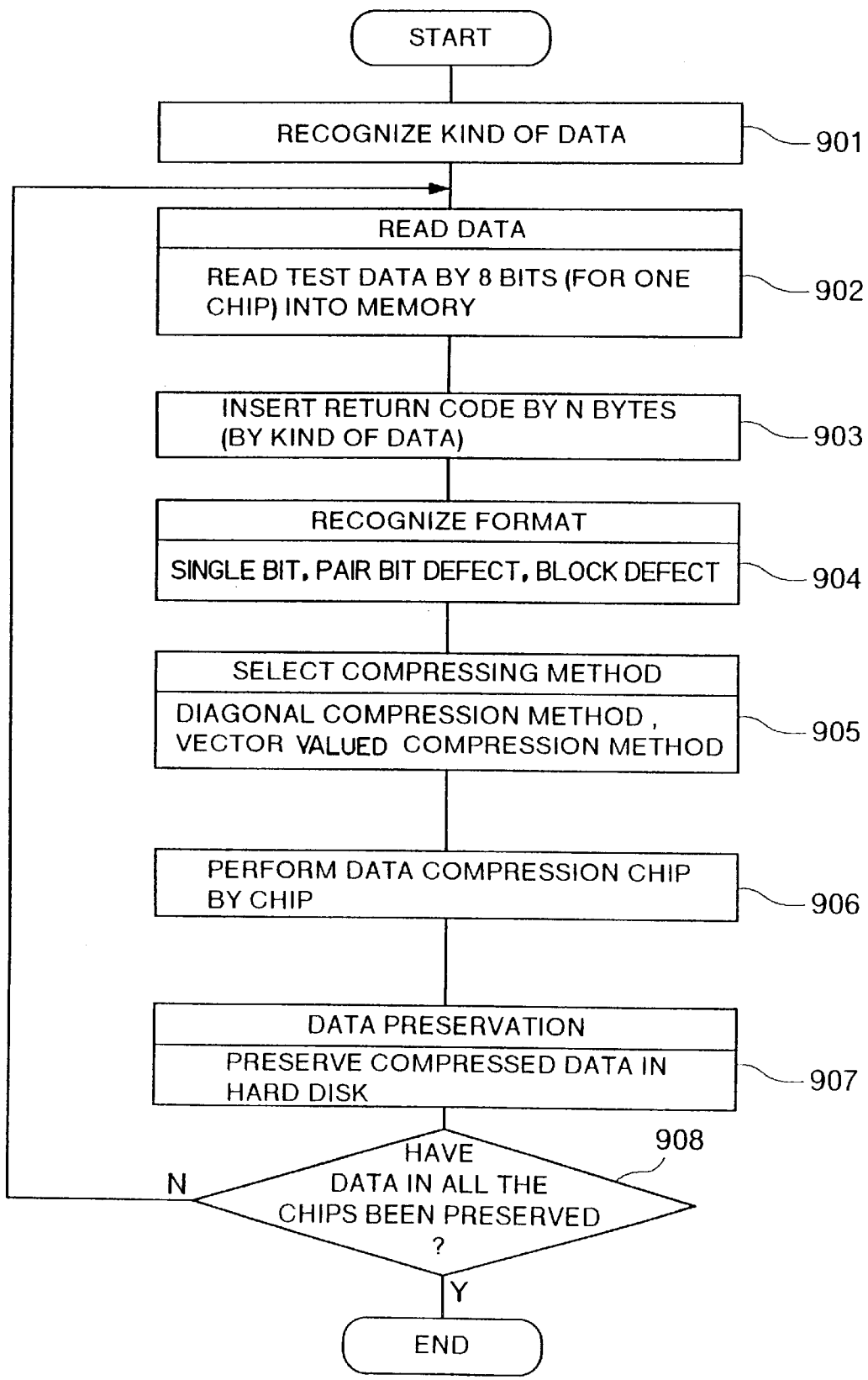
FIG. 9 is a flow chart for explaining a routine for selecting the compression methods each in accordance with a chip.
Figure 10:
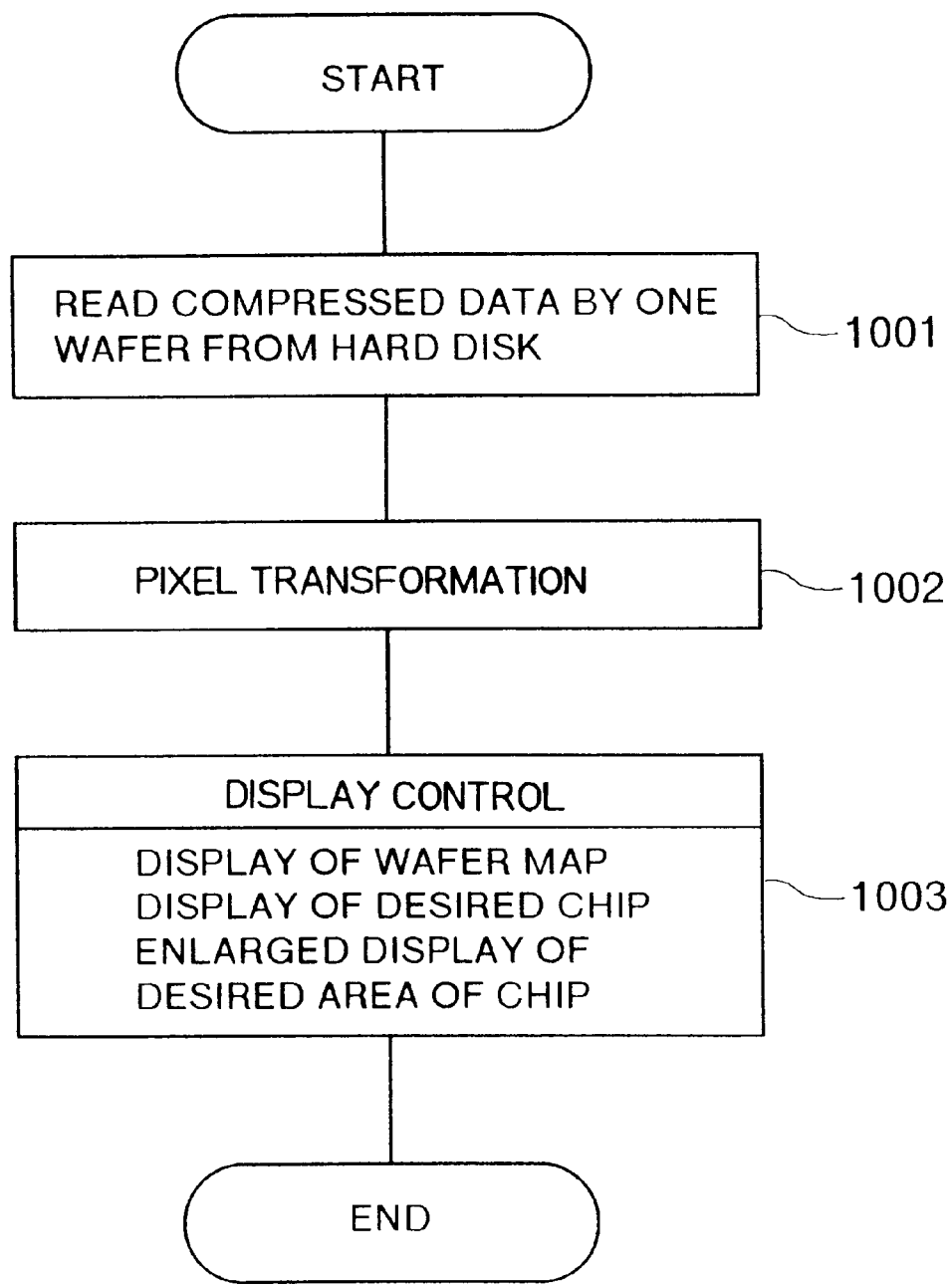
FIG. 10 is a flow chart showing a routine for restoring one-wafer data and displaying the data.

Referring to FIGS. 8 through 10, preservation of compressed data, restoration of data and display of data after the reading of data will be described below. Incidentally, these flow charts are used for compression, restoration and display with respect to one wafer.

FIG. 8 is a flow chart showing a routine for using several compression methods each in accordance with one fail bit format in a chip. In FIG. 8, first, the kind of data is recognized (step 801). Then, test data are read by eight bits onto memory (step 802). Then, a return code is inserted by every N bytes to give two-dimensional coordinates to the data (step 803). In this step, N represents the number of bits arranged laterally in a chip, and the positions into which return codes are inserted vary in accordance with the kind of data.

Then, the fail bit format in the chip is recognized (step 804).

FIG. 32 shows main formats of fail bits. A format in which a fail bit is surrounded by good bits as represented by (1) in FIG. 32 is defined as "isolated point". A format in which two fail bits are continued in the y direction as represented by (2) in FIG. 32 is defined as "lengthwise pair bit defect". A format in which two fail bits are continued in the x direction as represented by (3) in FIG. 32 is defined as "broadwise pair bit defect". A format in which N (N>2) fail bits are continued in the y direction as represented by (4) in FIG. 32 is defined as "lengthwise line defect". A format in which N (N>2) fail bits are continued in the x direction as represented by (5) in FIG. 32 is defined as "broadwise line defect". A format in which fail bits are collected in the form of a rectangle as represented by (6) in FIG. 32 is defined as "block defect".

Then, a compression method is selectively used in accordance with the recognized format (step 805).

Because bit-by-bit analysis is performed in this system, compression methods in which data can be restored perfectly are used in the case of compression of test data. Data can be restored perfectly by the following two compression methods.

(1) Diagonal Compression Method

Figure 33:
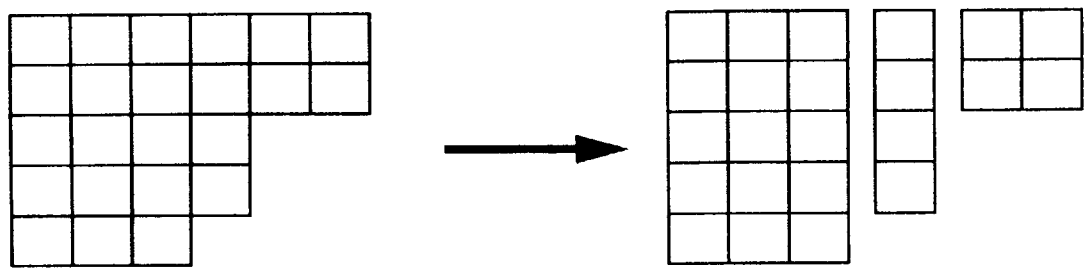
FIG. 33 is an explanatory view showing an example of diagonal division.

As shown in FIG. 33, in this method, first a cluster of fail bits is separated into several rectangles. Then, fail bit data in each of the rectangles are compressed. With respect to the way of taking data, the coordinates of diagonal points in the rectangle are set as data values (x1, y1, x2, y2) as represented by (6) in FIG. 32. In the case where "line defect" or "pair defect" is generated in the separated rectangle, the coordinates of the leading bit in the "line defect" and the coordinates of the last bit in the "line defect" are used. In this case, each of x and y is provided as two-byte data. In the case where "isolated point" is generated, the way of taking data is made to be different from the data taking way used in the other formats, that is, only the coordinates (x, y) of the fail bit are used as data values.

(2) Vector-valued Compression Method

Figure 34:
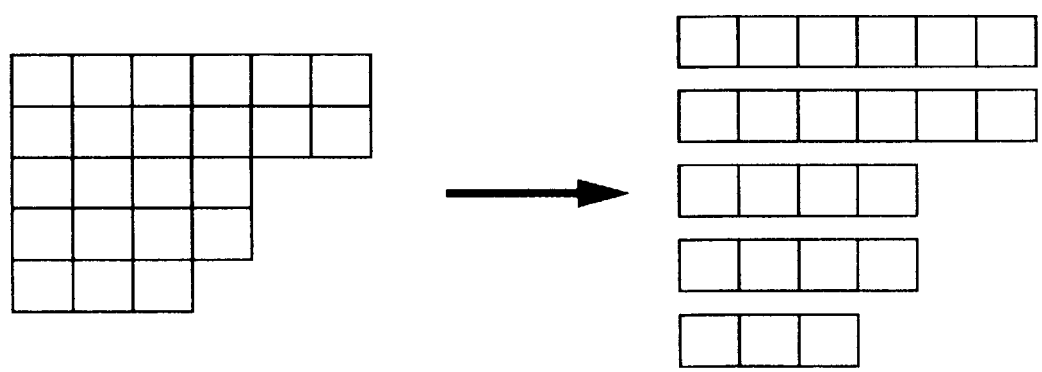
FIG. 34 is an explanatory view showing an example of vector-valued division.

As shown in FIG. 34, in this method, a cluster of fail bits is separated into several line defects. The coordinate (x, y) of the leading bit in each of the line defects and the number k of fail bits constituting the line defect are used as data values. That is, data are compressed in the form of (x, y, k) as represented by (4) and (5) in FIG. 32. In this case, each of x, y and k is provided as two-byte data. Incidentally, in the case where "isolated point" is generated in the separated line detect, the coordinates (x, y) of the fail bit are used as data values in the same manner as in the diagonal compression method.

After data are then compressed by the selected compression method (step 806), a judgment is made as to whether compression of all data in the chip is completed or not (step 807). If compression of all data is not completed, the procedure in and after the step 803 is repeated.

When compression of all data is completed as described above, one-chip compressed data are preserved in a hard disk (HD) which is an internal storage device (step 808). Then, a judgment is made as to whether preservation of compressed data with respect to all chips is completed or not (step 809). If the preservation is not completed, the procedure in and after the step 802 is carried out again.

Referring to FIG. 9, a schematic procedure from selection of a chip-by-chip compression method to preservation of compressed data will be described below. The procedure from step 901 to step 904 is the same as the procedure from the step 801 to the step 804 in FIG. 8. In the wake of the step 904, a compression method is selected (step 905). That is, in the case where the total capacity of line defects in one chip before compression is large compared with the other formats, the vector-valued compression method is selected. In the case where the total capacity of block defects before compression is large, the diagonal compression method is selected. In the case of "isolated point", either method may be selected because the form of data to be preserved is (x, y) irrespective of the method. In this embodiment, the diagonal compression method is selected for convenience sake.

After data compression is performed, the compressed data are preserved in the HD (steps 906 and 907). Unless preservation of one-wafer data is completed, the procedure of from the step 902 to the step 907 is repeated (step 908).

Referring to FIG. 10, restoration of compressed data and display of restored data will be described below. Through the following data processing, the human operator can display the test data on the display unit and can analyze the distribution of fail bits, or the like.

In FIG. 10, one-wafer compressed data are read from the HD (step 1001) and subjected to pixel transformation for high-speed displaying (step 1002). This is a process for compressing an image by using the compressed data directly to display the whole wafer as one scene. For example, in the case of "block defect" data, each of the coordinates of diagonal points in the compressed data is divided by the number of bits per one pixel to thereby calculate coordinates on the CRT. The coordinates thus calculated are displayed (step 1003).

How to display fail bits in a chip and how to analyze the fail bits will be described below.

The human operator retrieves fail bit data concerned with a desired wafer from the FB data base 107*b* by designating the sort name, lot number, wafer number, and so on, and displays the fail bit data on the display unit 200*a*. FIGS. 12 to 15 show display formats in this case.

Figure 13:
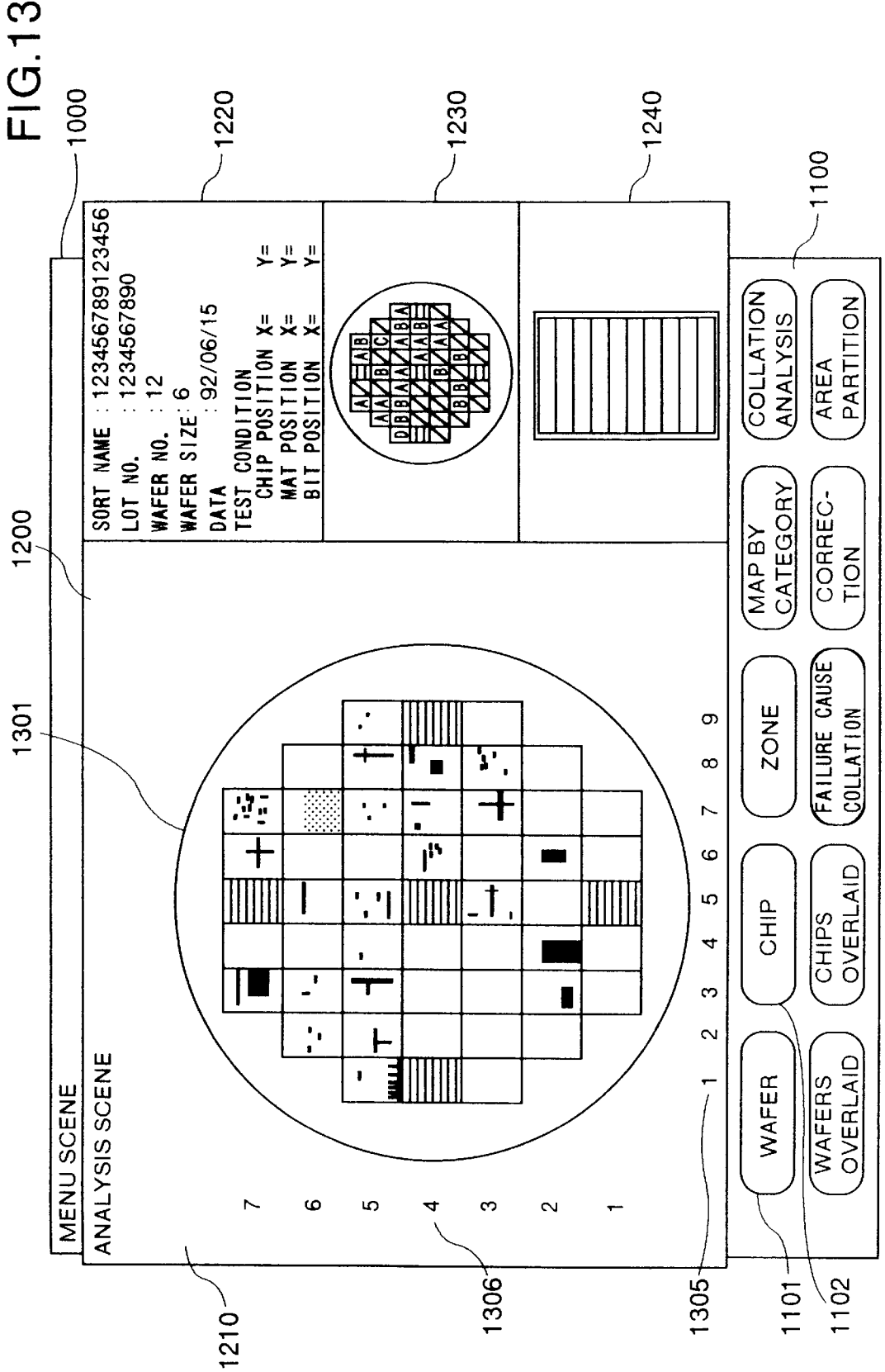
FIG. 13 is an explanatory view showing an example of the distribution of fail bits on a wafer as displayed on the display unit.

FIG. 12 shows the structure of a scene displayed on the display unit in this system. As shown in FIG. 12, the analysis scene in this system is mainly separated into four. Specifically, for example, as shown in FIG. 13, a portion to be analyzed is displayed in the main scene 1210. Data (the sort name, lot number, wafer number, wafer size, etc.) concerned with the subject of analysis and tester measurement conditions (source voltage, operating temperature, access time, etc.) are displayed in the subsidiary scene 1220. Category (classification applied to chips in the wafer for inspection) in the wafer, and so on, are displayed in the subsidiary scene 1230. The arrangement of mats in each chip, and so on, are displayed in the subsidiary scene 1240. Further, subsidiary windows may be opened as occasion demands. In this embodiment, this analysis scene 1200 is displayed as a standard scene simultaneously with the menu scene 1000 without the necessity of special designation when the menu scene 1000 is displayed.

An advantage given by display of tester measurement conditions in the subsidiary scene 1220 will be described now. Failures of semiconductors can be roughly classified into two groups. That is, one group is caused by trouble in the setting of standard values of the tester measurement conditions such as source voltage, measurement temperature, etc. The other group is caused by trouble in the production process. In the former, it is important to pursue the cause of failure as to what conditions make the number of failures increase or decrease in the case where a failure occurs though the measurement conditions are set to standard values. Therefore, test conditions, and so on, are displayed in the subsidiary scene 1220.

Because the display of the conditions makes a judgment clear as to whether the measurement conditions are set to standard values or unstandard values, analysis can be performed efficiently. If there is any fail bit though the measurement conditions are set to standard values, it is thought of that the failure is caused by shortage of the margin of the voltage of power supply.

On the contrary, if there is no fail bit generated newly though the standard value of the voltage of power supply is changed, values of the other measurement conditions are changed successively and measurement is performed. If results obtained from all measurements are equal to each other though values of the measurement conditions are changed, it is thought of that the fail bits are caused by trouble in the production process such as particles, defects, and so on.

Figure 14:
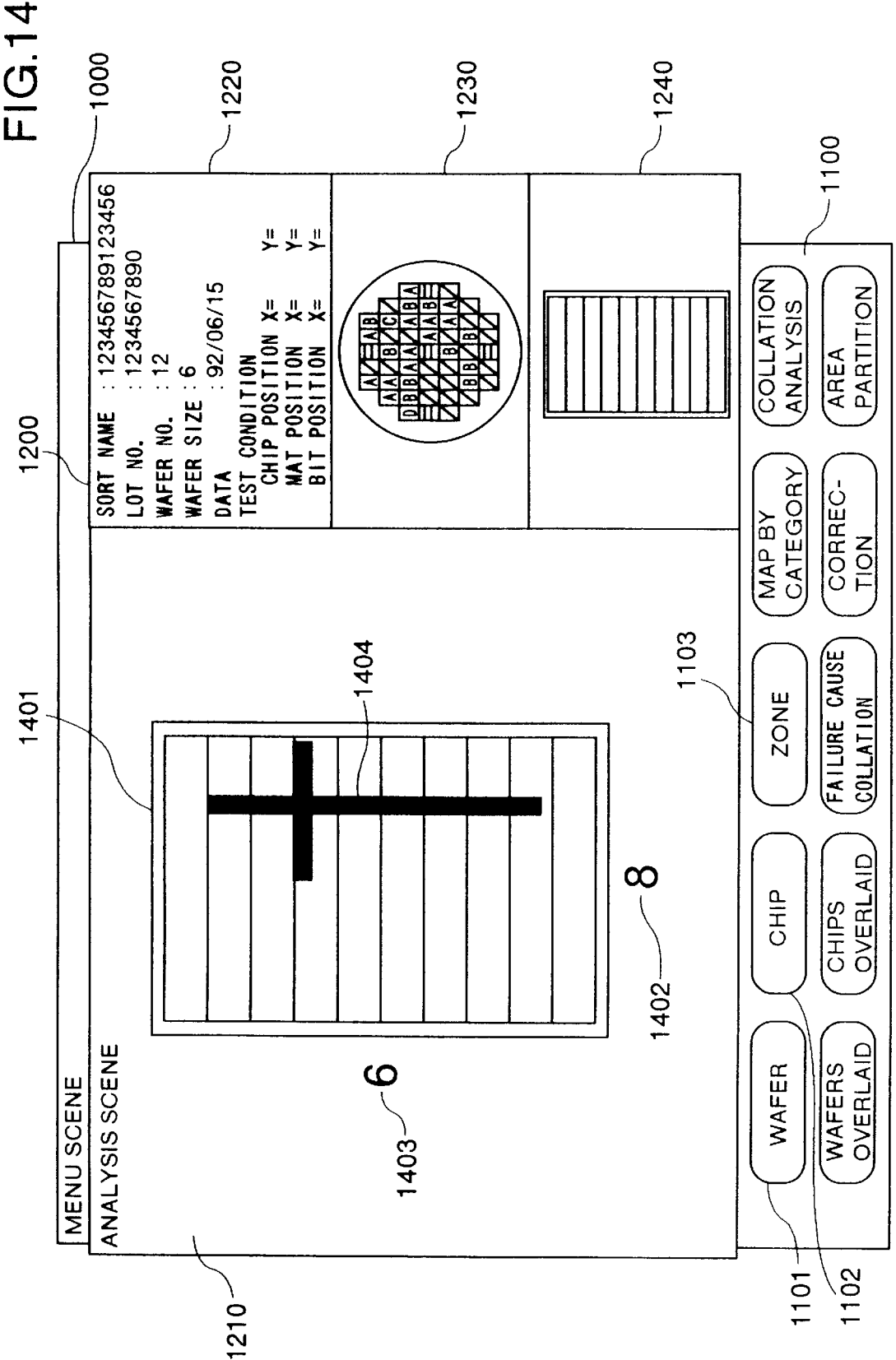
FIG. 14 is an explanatory view showing an example of the distribution of fail bits on a chip as displayed on the display unit.
Figure 15:
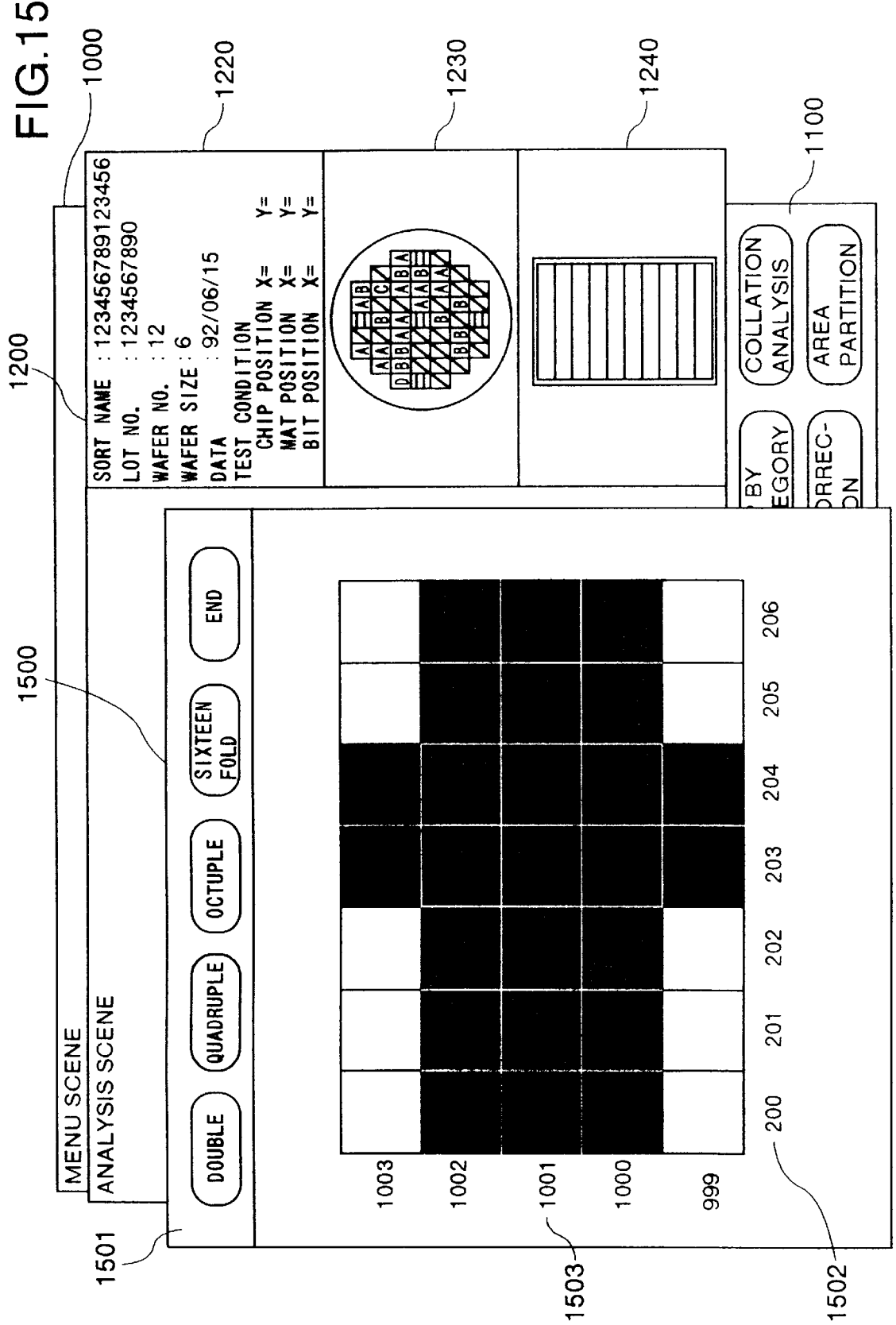
FIG. 15 is an explanatory view showing an example of the distribution of fail bits in a chip as enlargedly displayed on the display unit.

Referring to FIGS. 13 through 15, failure analysis will be described below practically by way of specific example.

FIG. 13 is a view showing an example of the distribution of fail bits on a wafer as displayed on the display unit. FIG. 14 is a view showing an example of the distribution of fail bits in a chip as displayed on the display unit. FIG. 15 shows the distribution of fail bits in a partial area of a chip as enlargedly displayed on the display unit.

When an operator points "wafer display" 1101 from selection items 1100 in the menu scene 1000 in which the analysis scene is displayed, a wafer whole image 1301 is displayed in the main scene 1210 as shown in FIG. 13. The distribution of fail bits in each chip is displayed in the wafer whole image 1301. Further, data such as a sort name, lot number, wafer number, wafer size, concerned with the subject of analysis and tester measurement conditions, such as source voltage, operating temperature of memory, access time, are displayed in the subsidiary scene 1220. Category (classification applied to chips in the wafer for inspection) in the wafer, and so on, are displayed in the subsidiary scene 1230. The arrangement of memory mats in each chip, and so on, are displayed in the subsidiary scene 1240.

An operator selects "chip display" 1102 from selection items 1100 in the menu scene 1000 and points a desired chip from the subsidiary scene 1230 by using a mouse or the like. When the desired chip is pointed, a chip whole image 1401 designated is displayed in the main scene 1210 as shown in FIG. 14. The distribution 1404 of fail bits in the chip is displayed in the chip whole image 1401.

In the display in FIGS. 13 and 14, the oriented flat side (the flat lower portion of the wafer) and the left side are set as the X axis and the Y axis, respectively, and the point of intersection of the X and Y axes is set as the origin. Further, numbers indicating the positions of chips on the wafer are displayed as represented by the reference numerals 1305 and 1306 in the case of "wafer display" in FIG. 13 or as represented by the reference numerals 1402 and 1403 in the case of "chip display" in FIG. 14, by which the positions of chips in the wafer displayed are made clear to the analyzing person.

When an operator intends to enlarge a portion in a scene such as "wafer display", "chip display" or the like, the portion is enlargedly displayed as shown in FIG. 15. When the human operator points "zoom" 1103 from selection items 1100 by using a mouse in order to enlarge a portion in "wafer display" or "chip display", an enlarged display scene 1500 is opened newly as shown in FIG. 15. When the magnification of enlargement is to be further increased, one button selected from magnification buttons 1501 in the upper portion of the scene is pointed by using a mouse or the like to thereby make it possible to change the magnification of enlargement freely. Because the coordinates (X, Y) 1502 and 1503 based on the design information are displayed on the scene, the positions of fail bits can be confirmed easily. When the magnification of enlargement is changed, the display of the coordinates is changed in accordance with the change of the magnification of enlargement.

Categorization of fail bits will be described below.

The distribution of fail bits can be classified into several patterns on the basis of a judgment as to whether the distribution of fail bits is periodic or nonperiodic, a judgment as to whether a pattern of fail bits abuts on a peripheral circuit or not, and a judgment as to whether the direction of the pattern is lengthwise or broadwise. For example, the confirmation as to whether the fail bit pattern abuts on the peripheral circuit or not, becomes useful for a judgment as to whether the failure is caused by trouble in the peripheral circuit or by trouble in the memory cell per se. Further, a data line and a word line are present in each memory mat. Accordingly, difference between causes of failures can be found on the basis of discrimination between lengthwise direction and broadwise direction even in the case where the failures have the same shape as long as account of the direction of the pattern is taken.

Therefore, patterns of generation of fail bits are classified in relation to the causes of failures so that an unskilled operator can analyze estimation of the cause of the failure easily.

Figure 16:
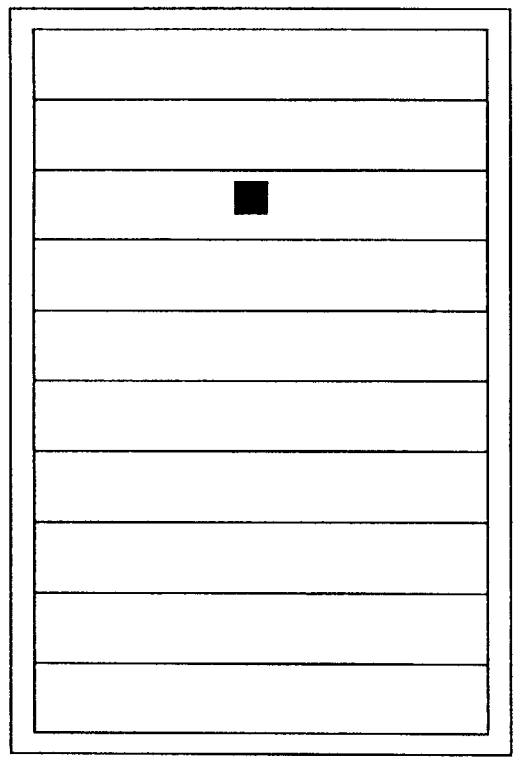
FIG. 16 is an explanatory view showing an example of the distribution of fail bits in a chip.

Specifically, in the case of FIG. 16, a fail bit is generated so as not to be in contact with the peripheral circuit. It is thought of that this is based on the deposition of foreign matter (particles) on a memory cell in which the failure has occurred.

Figure 17:
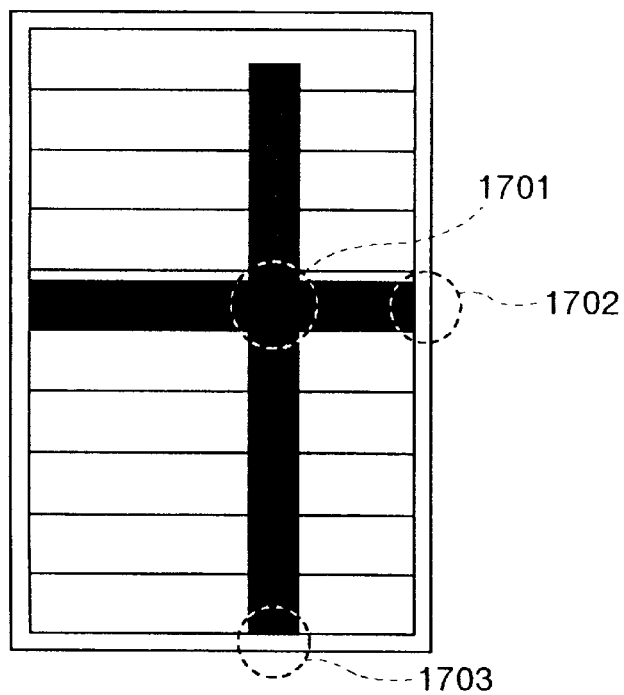
FIG. 17 is an explanatory view showing an example of the distribution of fail bits in a chip.

Further, in the case of FIG. 17, fail bits are generated in the form of a cross. Further, the fail bits are in contact with the peripheral circuit. It is thought of that the failure is caused by short-circuiting at the intersecting portion 1701 or by short-circuiting at the peripheral circuits 1702 and 1703.

In the case where a plurality of causes are thought of correspondingly to one pattern as described above, causes are related to the pattern in order so that priority is given to the cause of highest possibility. The relating of causes to the pattern is based on the past analysis results.

Figure 19:
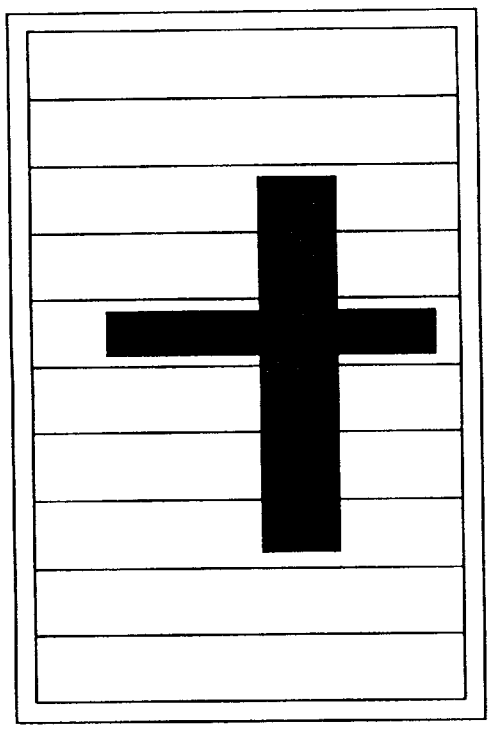
FIG. 19 is an explanatory view showing an example of the distribution of fail bits in a chip.
Figure 20:
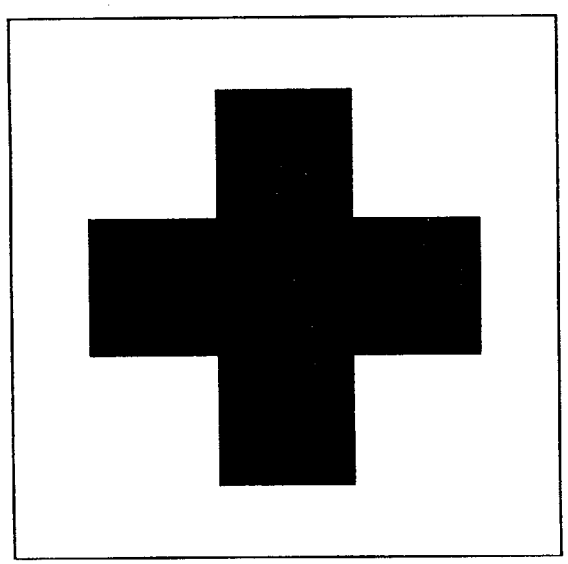
FIG. 20 is an explanatory view showing an example in which a pattern of distribution of fail bits generated in a chip is displayed by category.

FIG. 18 shows an example of a failure cause list 1800 in which patterns of generation of fail bits and causes of failures are collected on the basis of the aforementioned rule. The category 1801 displayed in the failure cause list shown in FIG. 18 means visual expression of classified fail bit patterns easy to understand. That is, the category 1801 means coding of the patterns of generation of fail bits. When, for example, a cross line pattern which is not in contact with any peripheral circuit is given as shown in FIG. 19, a category pattern as shown in FIG. 20 is obtained.

As described above, relations between fail bit patterns and causes of failures are preserved in the failure cause know-how data base 108 shown in FIG. 1 in the form of files separated by kinds. Further, in the case where failure category is generated newly, the category of the failure, the cause of the failure, and so on, can be registered additionally and successively in the failure cause know-how data base 108.

The function of a category map using the category patterns will be described below. This function is used for macro-analyzing the situation of generation of fail bits efficiently and accurately, so that the situation of generation of fail bits generated in an arbitrary area is analyzed by using the category of fail bits classified as described above. The category is displayed by a rule in which a fail bit pattern generated most frequently in an arbitrary area is used as a representative pattern in the area.

Figure 21:
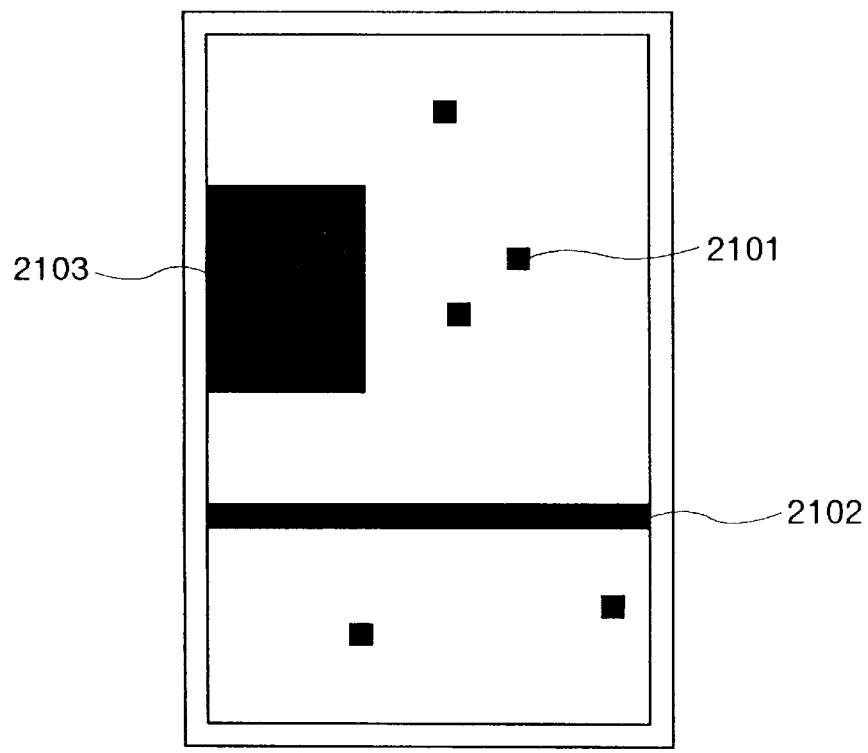
FIG. 21 is an explanatory view showing an example of the distribution of fail bits in a chip.
Figure 22:
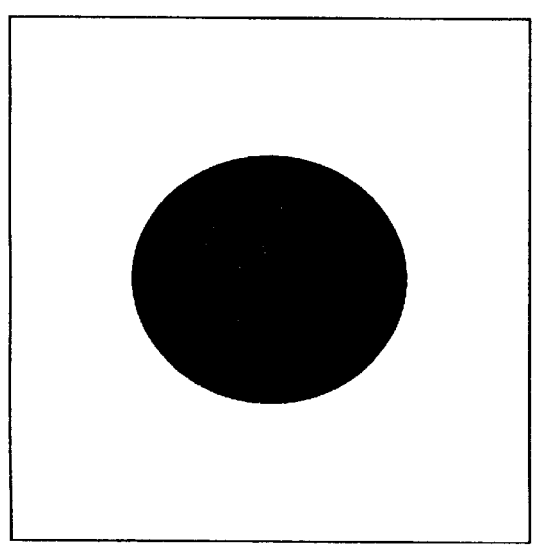
FIG. 22 is an explanatory view showing an example in which a representative pattern extracted from the pattern of distribution of fail bits in a chip is displayed by category.

When, for example, fail bits as shown in FIG. 21 are generated, the representative pattern in this area is a single bit 2101 because five single bits 2101, one lengthwise line 2102 and one block defect 2103 are present. In this case, the representative pattern is expressed in category as shown in FIG. 22. Incidentally, in the case where fail bit patterns are equal in the number of generation of fail bits though the fail bit patterns are different, the pattern to be displayed is determined in accordance with the area of the pattern and the degree of importance in measures against failures.

A method of pursuing the cause of a failure by using the category map generated in accordance with the aforementioned rule will be described below.

Figure 23:
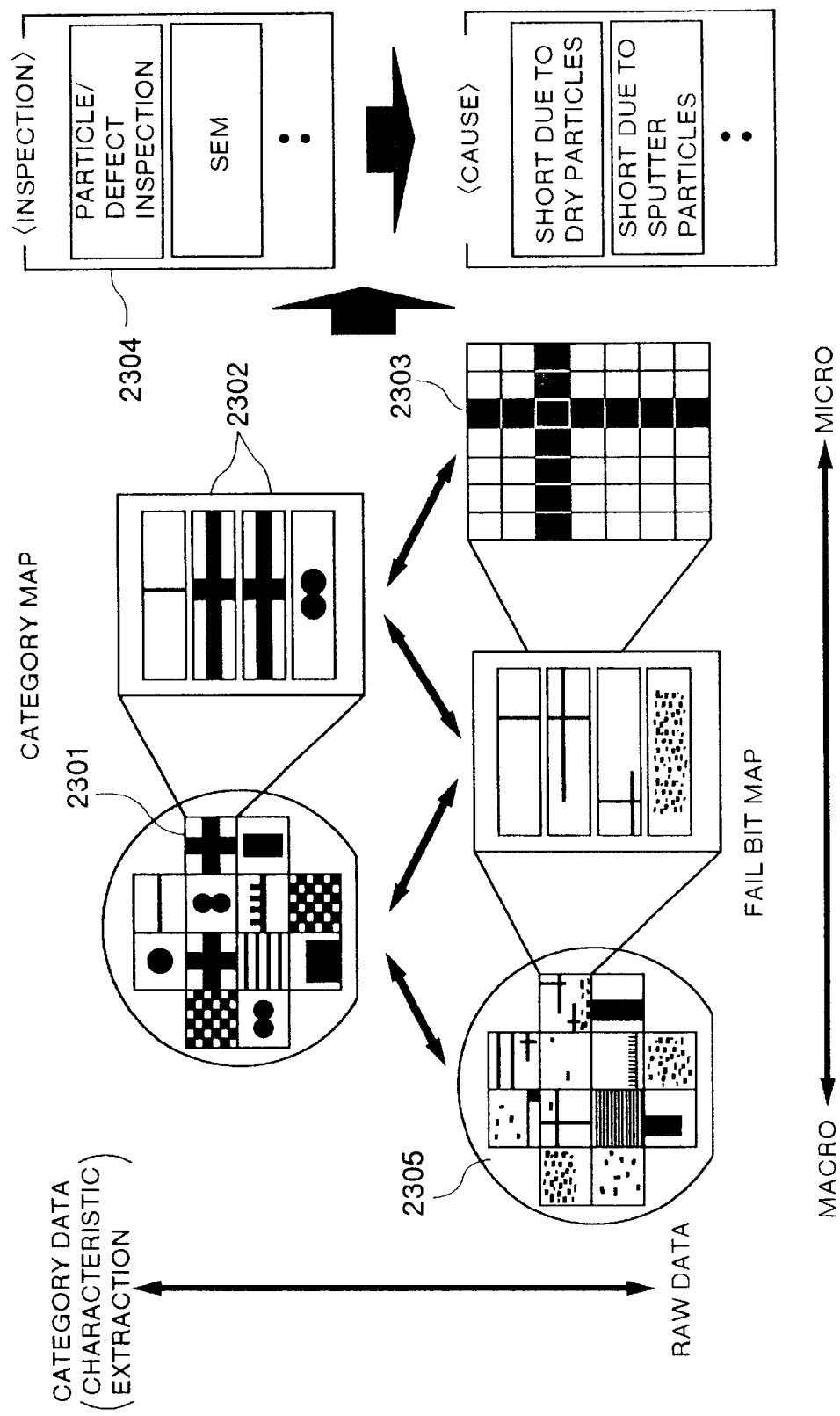
FIG. 23 is an explanatory view showing category maps displayed in the display unit.

FIG. 23 shows an example of the category map. First, on the whole wafer, the situation of generation of fail bits is grasped. Then, the chip in which category attracting attention is displayed is confirmed as to what memory mat in the chip has generation of the category or as to what position in an arbitrary area has generation of the category. Further, the accurate position of the pattern attracting attention is confirmed by using a detailed fail bit map in which fail bits are plotted one by one.

In this analysis method, nothing but confirmation of the positions of generation is required after the cause of the failure is estimated in advance. Accordingly, extreme reduction of analyzing time is attained compared with analysis using only the fail bit map.

For example, in the case where attention is given to a cross pattern 2301, positions where such a cross pattern is generated are confirmed in the chip. Then, the mats 2302 in which the cross pattern 2301 is generated are subjected to detailed analysis by using the fail bit map 2303, so that the coordinates of the position where fail bits are generated are confirmed. There is a method comprising the steps of: feeding the coordinates to a scanning electron microscope or an inspection apparatus 2304 such as a particle inspection apparatus, a defect inspection apparatus, or the like; and performing further analysis to identify the cause of the failure to thereby take measures against the failure.

Because this system can display the fail bit map and the category map on the same and one scene, the category map and the fail bit map can be displayed speedily in accordance with the purpose of analysis so that the real distribution can be confirmed on the basis of the wafer map 2305 of fail bits while the situation of generation on the whole is grasped on the basis of the wafer 2301 of the category map.

Figure 24:
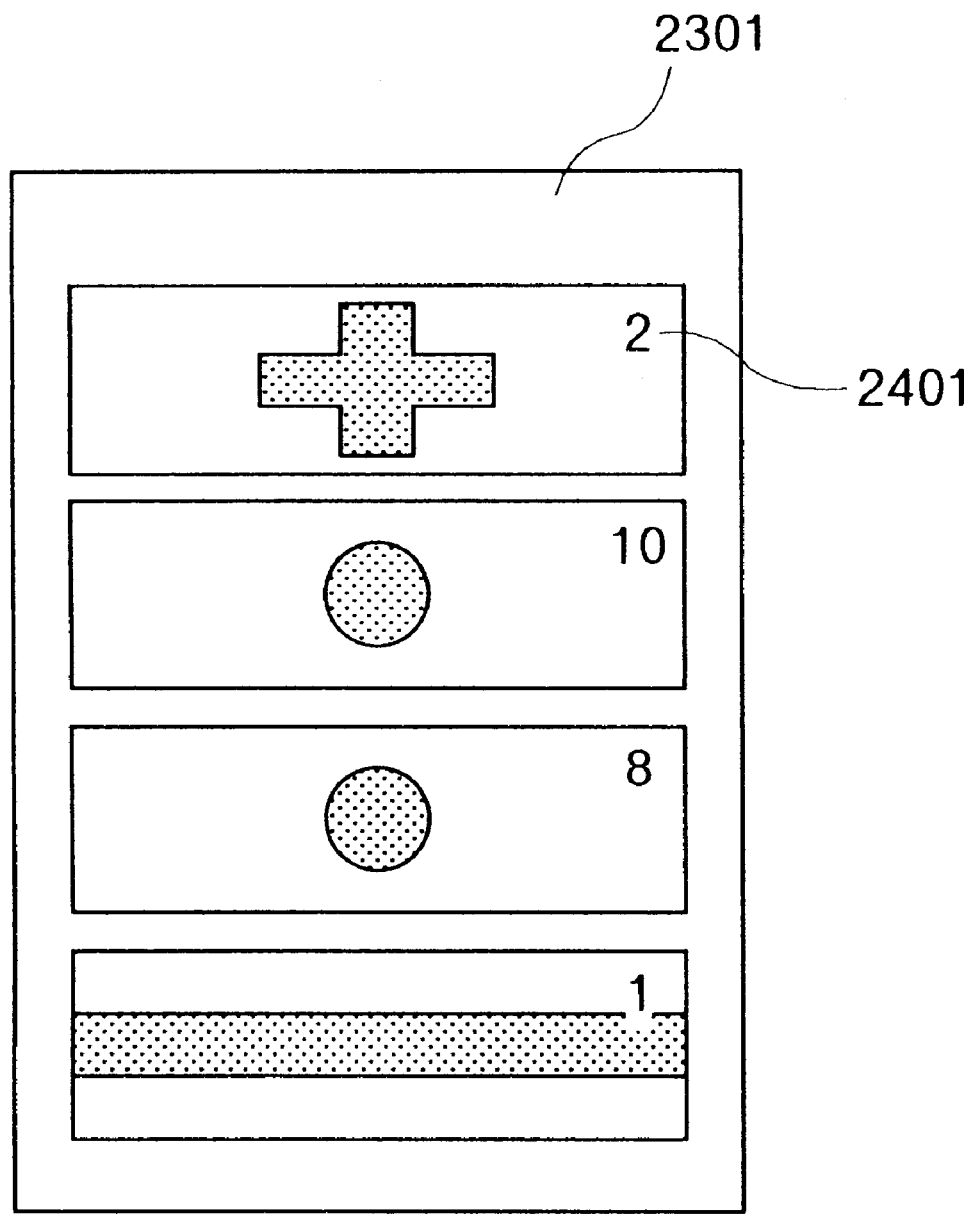
FIG. 24 is an explanatory view showing an example in which patterns of distribution of fail bits generated in a chip are displayed by category.

Further, in the case where the category map is displayed, the frequency 2401 of generation of the pattern (the number of patterns of the same) is displayed in the vicinity of each category pattern as shown in FIG. 24. Accordingly, the situation of generation of failures can be grasped without confirmation of the fail bit map in which fail bits are plotted one by one. The frequency of generation of the pattern is displayed in the wafer map, the chip map, or the like.

Not only the function of the category map makes it easy that a person performs analysis visually, but also recognition is performed easily in the case of automatic analysis using a camera or the like. Further, because the representative category is determined after the situation of all failures is confirmed, the category map is macro but accurate information.

The cause collation function of fail bit patterns will be described below.

This function can be used on the fail bit map or the category map. The method of collating the cause of the failure is as follows. When a category pattern on the map or the distribution of fail bits is pointed by using a mouse or the like and the failure cause collation function 1108 is selected, suitable failure causes are displayed.

Figure 25:
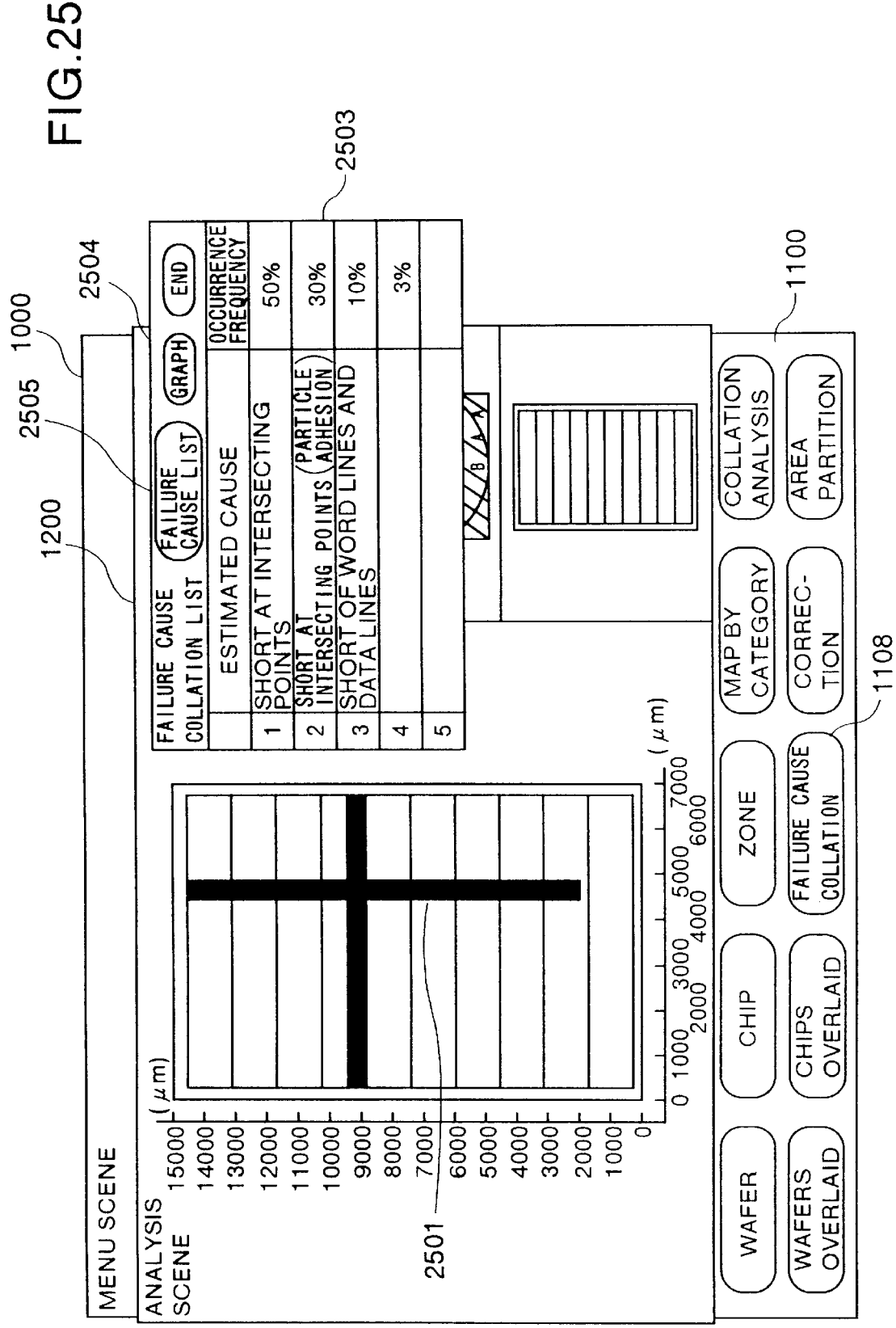
FIG. 25 is an explanatory view showing a failure cause collation list displayed in the display unit.
Figure 26:
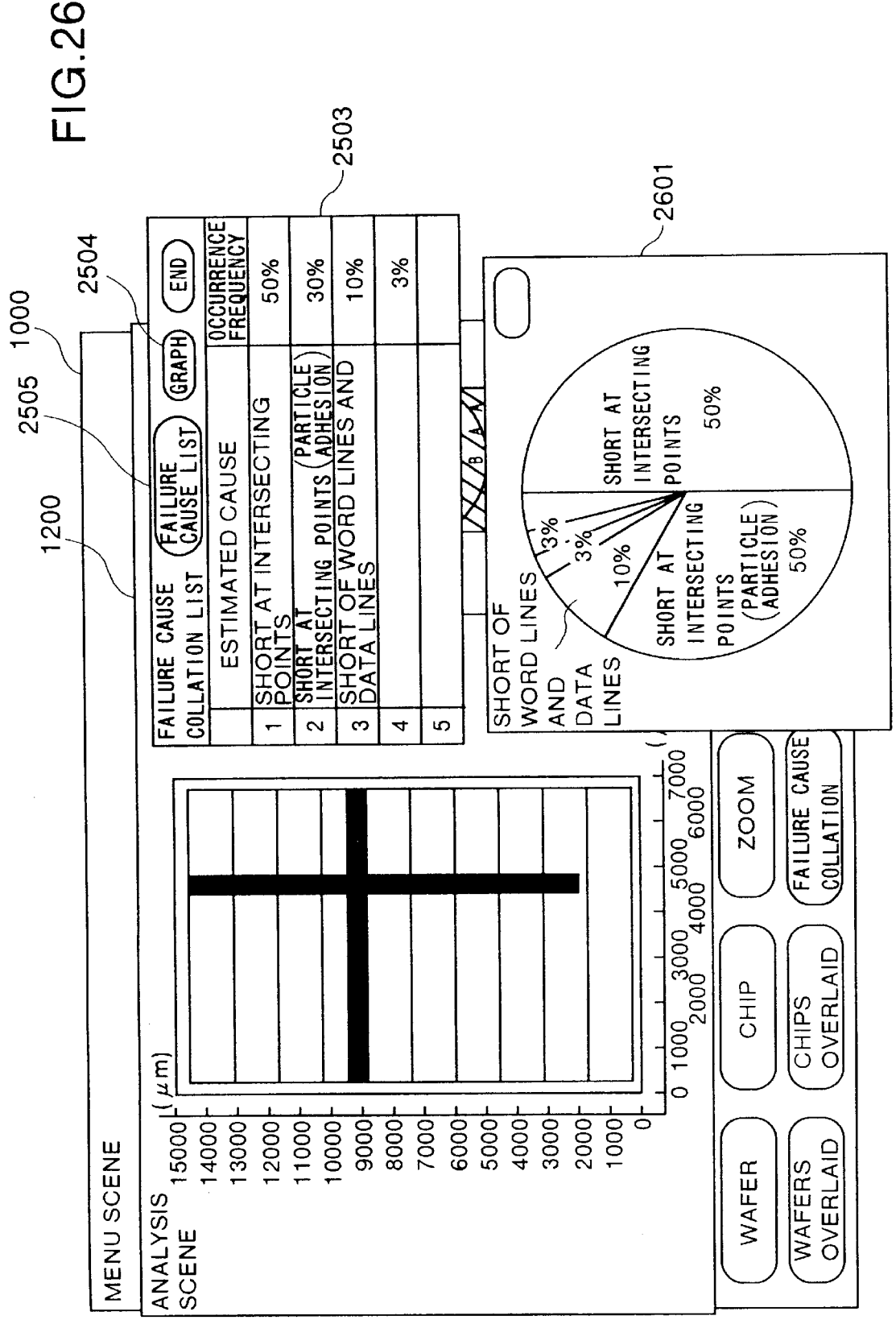
FIG. 26 is an explanatory view showing the case where failure cause items displayed in the display unit are expressed in a circular graph.

When, for example, the cause of the failure is collated by using the fail bit map, first a desired fail bit pattern 2501 is pointed from the fail bit map shown in FIG. 25 by using a mouse or the like and then "failure cause collation" 1108 is selected by using a mouse or the like. As a result, a subsidiary scene 2503 is opened newly, so that estimated failure causes are displayed in the form of a priority list. When "graph" 2504 shown in FIG. 25 is further pointed by using a mouse or the like, a graph scene 2601 in which the breakdown of the estimated causes of failures is expressed in a circular graph is displayed as represented by the reference numeral 2601 in FIG. 26.

Figure 27:
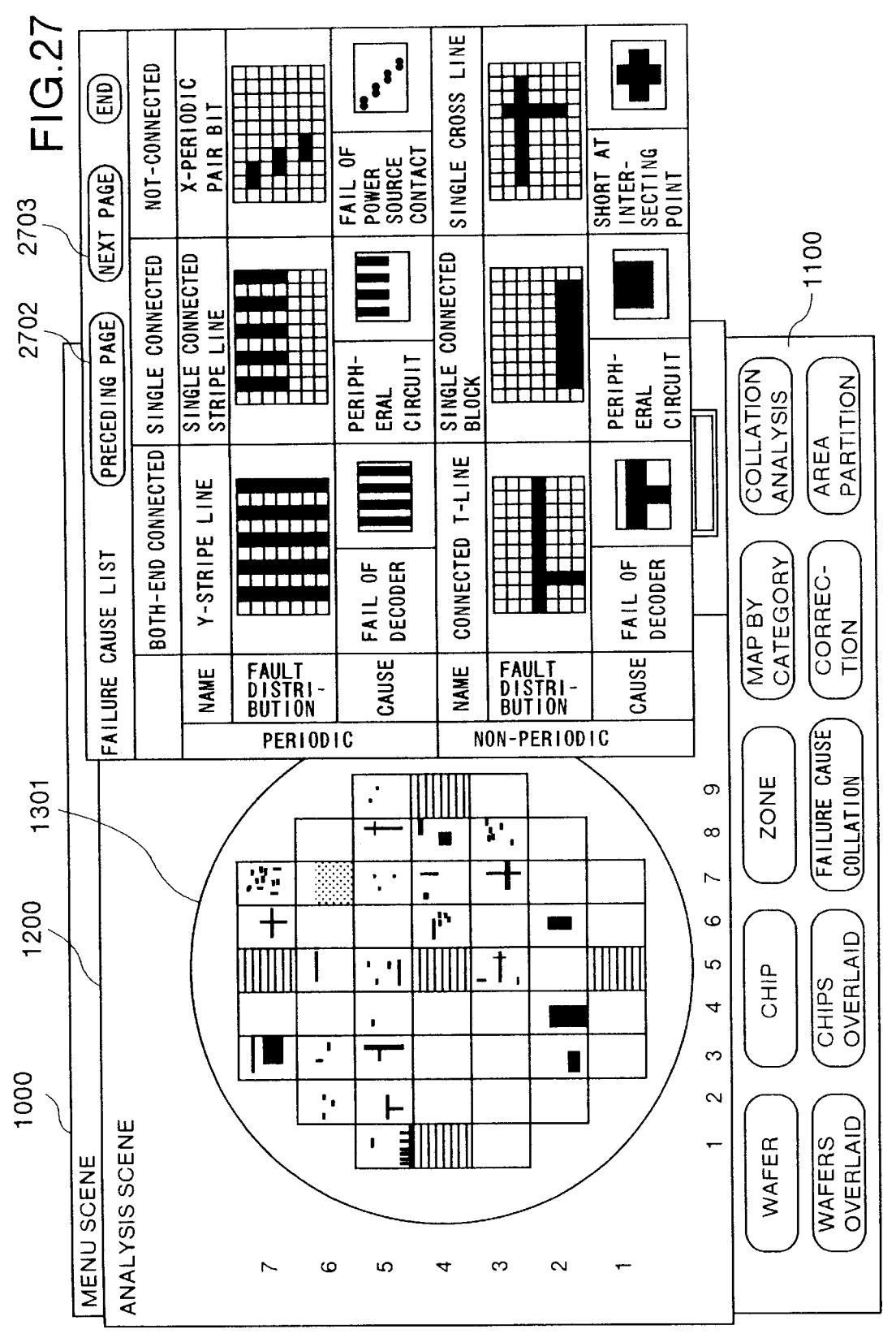

Further, when "failure cause list" 2505 is pointed, a table 2701 showing the correspondence or relations between category patterns and failure causes thereof is displayed as shown in FIG. 27. As the failure causes displayed at that time, causes of the highest priority at that time are determined for the correspondence on the basis of the past actual results. Accordingly, the causes of failures vary in accordance with the past situation. A desired failure cause can be retrieved by using the previous page 2702 and the next page 2703 in FIG. 27. The same rule is applied to the case of the category map.

The area partition function will be described below. This function is used for partitioning an arbitrary area into a plurality of areas, collecting the frequency of fail bit patterns classified as described above for each area and expressing results of the collection in numerical values. A method in which a human operator sets an area to be partitioned in advance is used as the method of partitioning the area. The method of setting the area to be partitioned is carried out by the following procedure.

Figure 28:
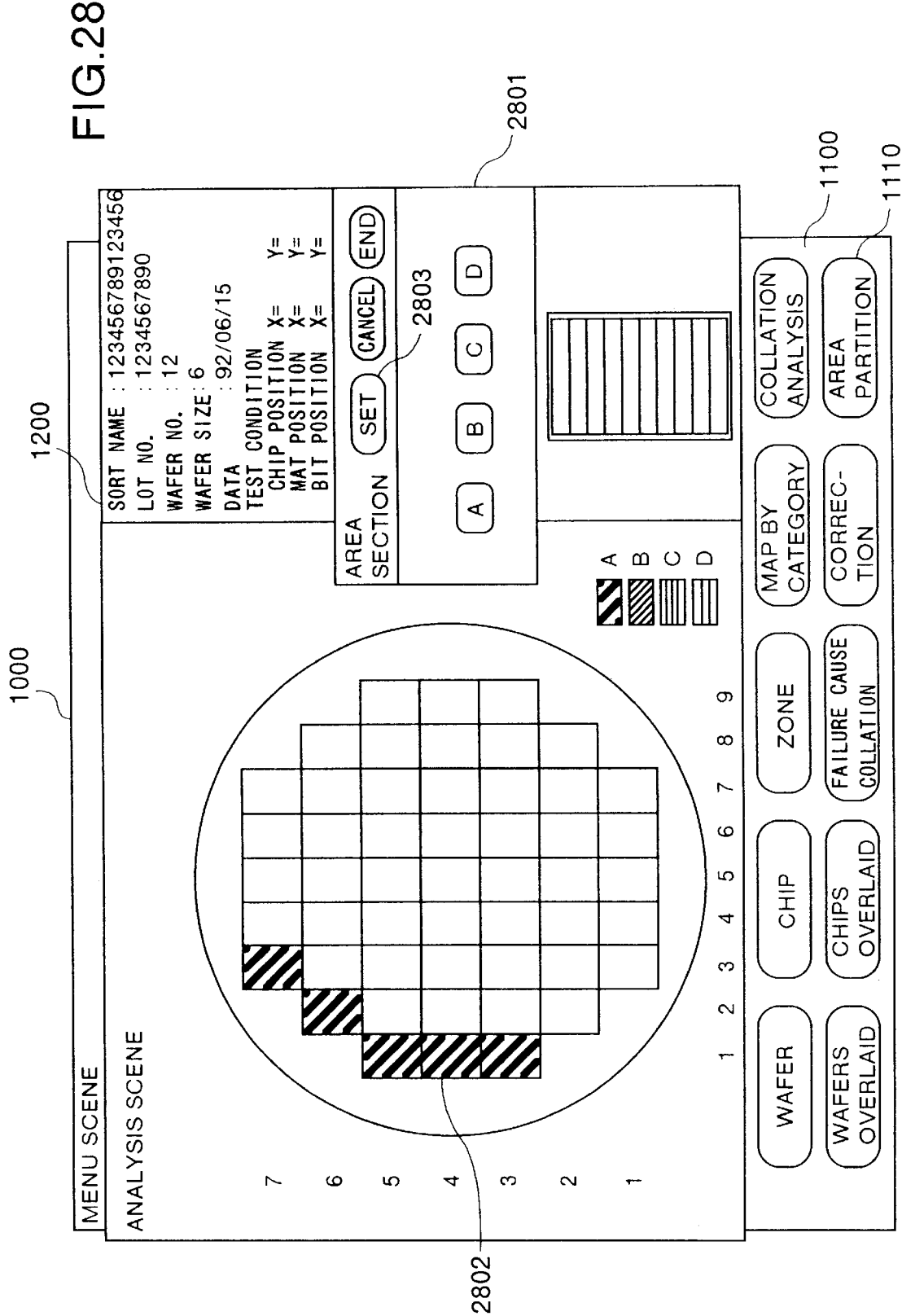
FIG. 28 is an explanatory view showing an area partition setting scene displayed in the display unit.

First, an operator points "sort name" in condition retrieval. Then, the operator points "area partition" 1110 to start the area partition setting function. As a result, a scene as shown in FIG. 28 is opened. One area is selected in an area section scene 2801 and then desired chips on the wafer map are pointed successively by using a mouse or the like.

When, for example, an area A is to be designated, first a button "A" in the area section scene 2801 is pointed by using a mouse or the like. Then, chips 2802 to be contained in the area A are pointed successively by using a mouse or the like. Areas B to D are set in the same manner as described above. After the setting of all chips is completed, "setting" 2803 is pointed so that for example the setting is registered in the design information data base 107*a*. If registration names are inputted at the time of registration, a plurality of area partition patterns can be registered by changing the set area to be partitioned. The same rule can be applied to partition of a chip or partition of an arbitrary area.

A procedure for using the area partition function will be described below.

Figure 29:
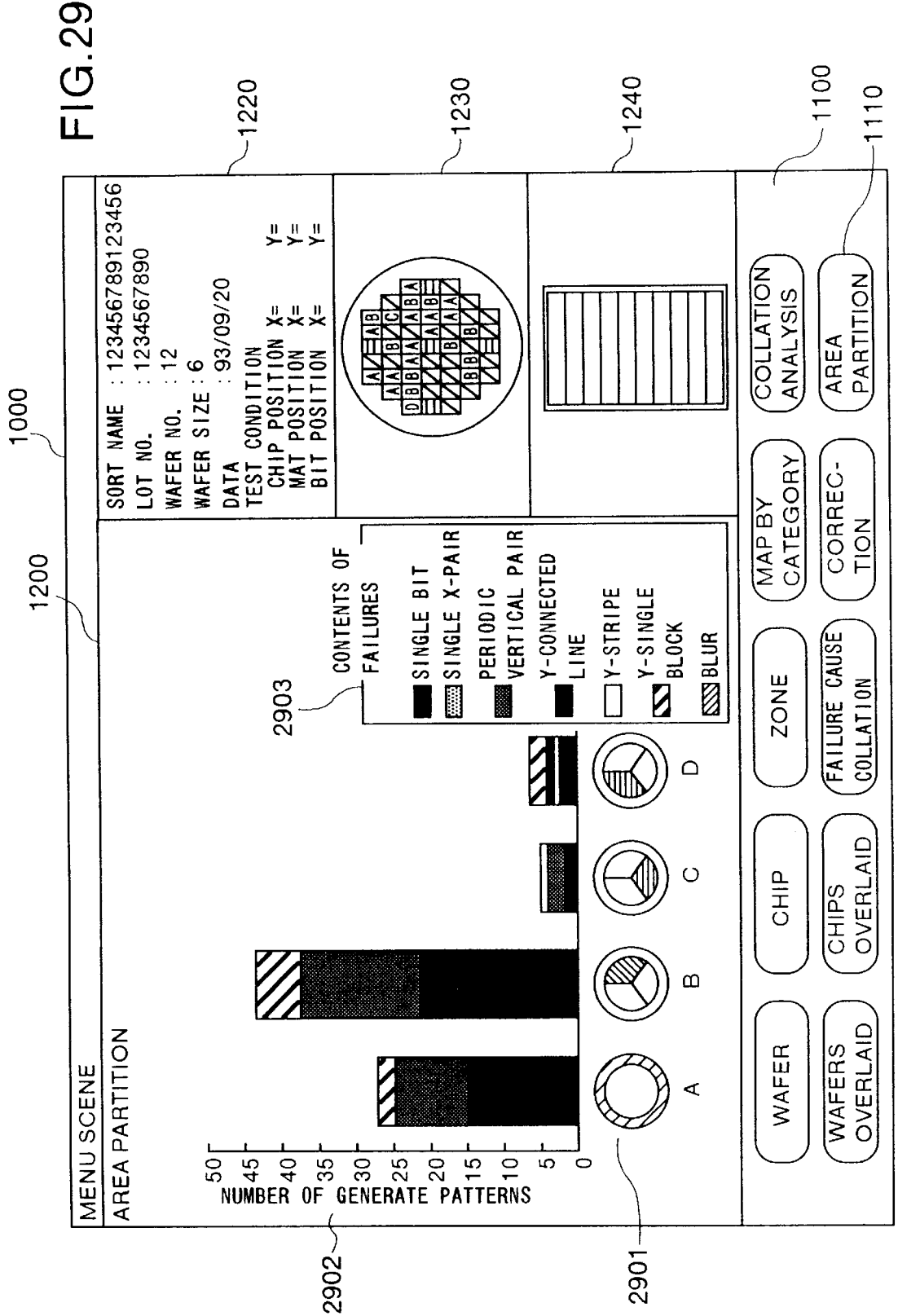
FIG. 29 is an explanatory view showing the situation of occurrence of failures in respective areas of a wafer as displayed in the display unit.

First, necessary conditions such as the sort name, lot number, are inputted by condition retrieval to call desired data. Then, "area partition" 1110 is pointed. As a result, the breakdown of patterns of the distribution of fail bits is expressed in a graph for each of the areas obtained by the partition as shown in FIG. 29. As the output of the graph, the frequency of generation of patterns and the number of generated patterns are displayed in the ordinate axis whereas information concerned with data separated by months, weeks, dates, lots, wafers, arbitrary areas, and so on can be outputted in the abscissa axis.

FIG. 29 shows an example of the output. The partitioned areas 2901 are taken in the abscissa axis, whereas the number 2902 of generation of patterns is taken in the ordinate axis. The way of looking at this graph is as follows. For example, on the whole of a wafer inspected on the date of 93/9/20, the respective numbers of patterns generated in the respective areas A to D are displayed. The contents 2903 of failures shown in the graph are displayed in the right lower portion of the scene. Although FIG. 29 shows the case where the ordinate axis is used for expressing the number of generated failures, the invention can be applied to the case where the ordinate axis is used in another mode for expressing the percentage of generation of failures.

According to this function, abnormality can be found at an early stage in the case where failures such as abnormality in an apparatus is generated locally.

A failure category transition graph function will be described below. This function makes it possible that the situation of fail bit generation patterns can be managed so as to be classified by wafers, lots, dates, weeks or months.

Figure 30:
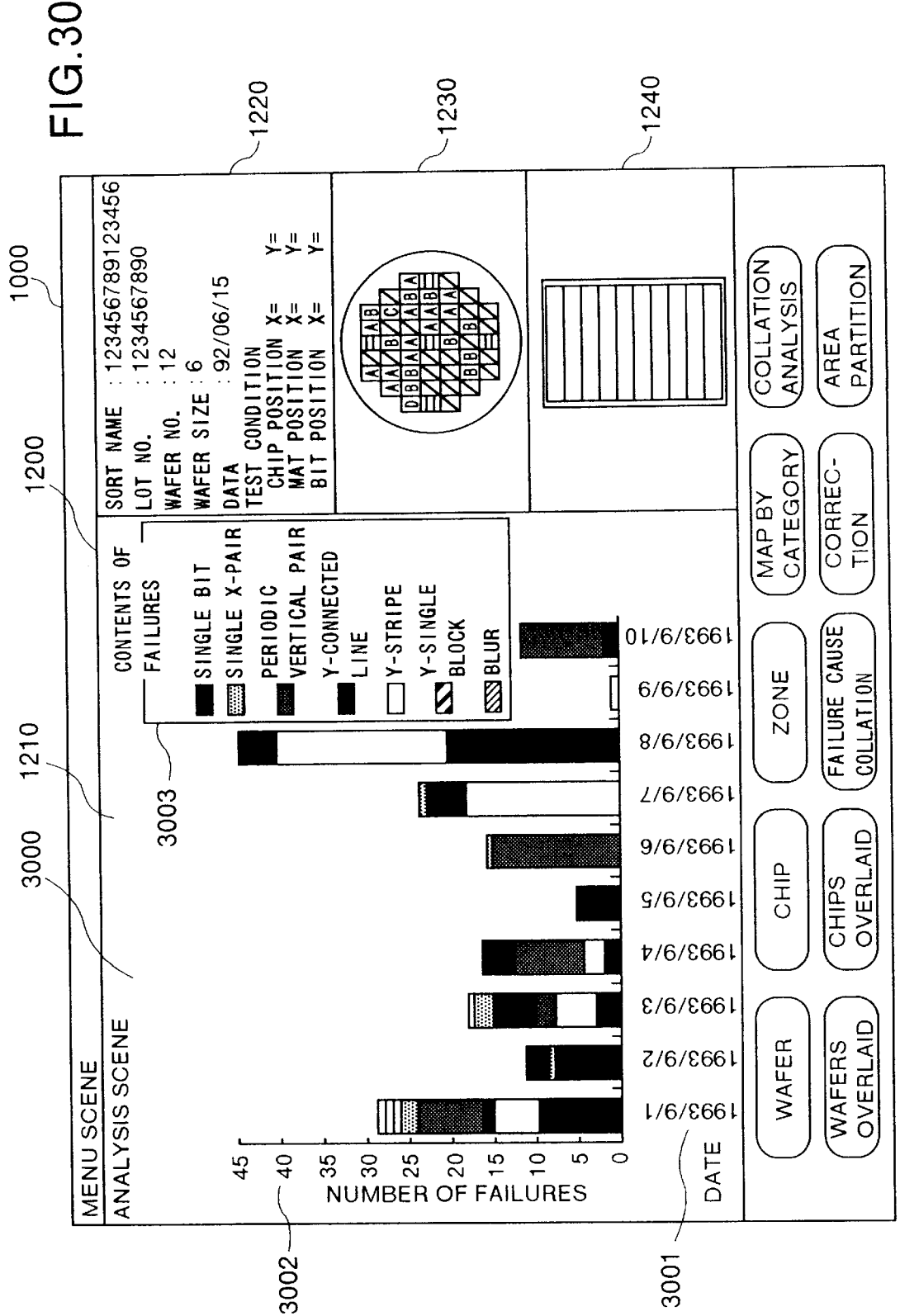
FIG. 30 is an explanatory view showing the situation of occurrence of failures separated by date as displayed in the display unit.

For example, in the case where the situation of generation of fail bits is to be analyzed so as to be classified by dates (93/9/1 to 93/9/10), first the human operator selects necessary conditions such as the sort name, term, lot number, etc. in the subsidiary scene 1220 by condition retrieval to search the FB data base 107b. As a result, a date transition graph 3000 in which data are classified by dates as shown in FIG. 30 is put out onto the main scene 1210. Dates 3001 are displayed in the abscissa axis, whereas the contents (unit: number) 3002 of failure patterns generated in the wafer inspected on each of the dates are displayed in the ordinate axis. The contents 3003 of respective failure patterns are displayed in the right lower portion of the scene. Although FIG. 30 shows the case where the ordinate axis is used for expressing the number of generated failures, the invention can be applied to the case where the ordinate axis is used in another mode for expressing the percentage of generation of failures.

The situation of generation of failures can be monitored every day by this function so that abnormal lots/wafers can be detected at the time of occurrence of abnormality by further analyzing a transition graph in which data are classified by lots/wafers. Because a process in which failures have occurred is identified by using the category map or fail bit map for further pursuing the cause of the failures so that the occurrence of abnormality is alarmed, a large number of failures can be prevented from occurring. Further, results of analysis can be fed back to the process in which failures have occurred, so that measures can be taken against the cause of the failures.

Next, description will be made as to a method of improving the yield of production of LSI by using the inspection data analysis system 101 and the FB analysis system 105 shown in FIG. 1 in combination. As described above, in the inspection data analysis system, results of particle inspection and results of defect inspection of product wafers flowing in a production line and results of final inspection of the product wafers are managed and analyzed.

On the other hand, in the FB analysis system, it is possible to count the respective numbers of classified failures generated on a wafer, as shown in FIGS. 25, 26, 27, 28 and 29.

Figure 31:
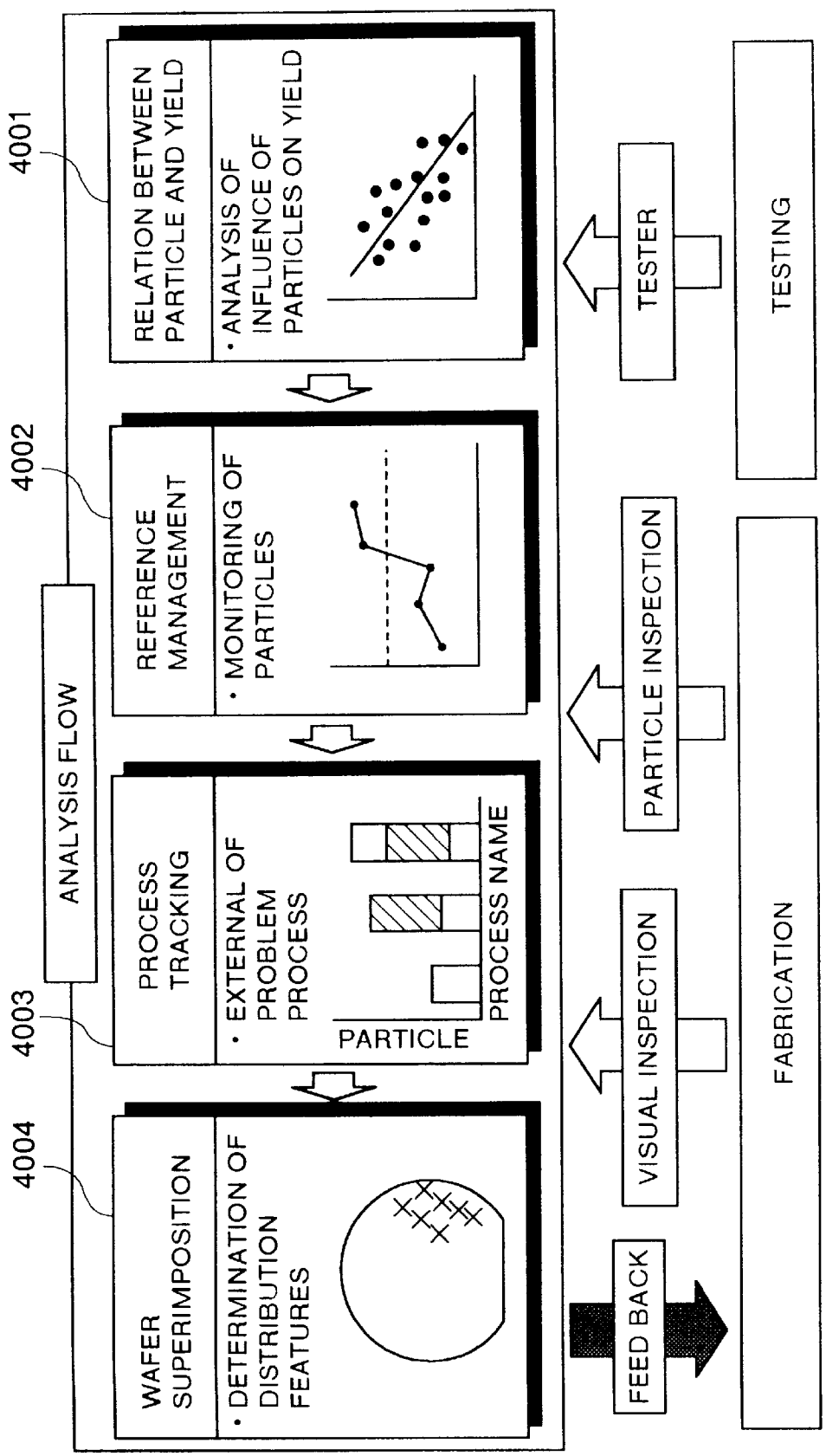
FIG. 31 is an explanatory view showing a process for specifying an abnormal step on the basis of semiconductor failure information and analysis of inspection data and for taking measures against the abnormality.

If the two systems are used in combination, correlations between the number of particles or defects on a wafer and the number of fail bit patterns can be taken easily as represented by the reference numeral 4001 in FIG. 31. In a graph designated by the reference numeral 4001, the abscissa axis shows the number of particles or defects and the ordinate axis shows yield (the percentage of good articles), the number of fail bit patterns or the percentage of failures, for example, obtained by dividing the number of fail bit patterns by the number of chips on the wafer. Correlations between the number of particles or defects on the wafer and the number of fail bit patterns can be obtained by the graph 4001. Accordingly, when the number of fail bit patterns generated is to be suppressed to be not larger than a desired level, the number of particles or defects to be managed can be set in accordance with the inspection process used.

The number of particles or defects is managed in accordance with the inspection process on the basis of this management criterion (4002). Then, some of the processes in which the number of particles or defects is out of the management criterion are selected and particle inspection or defect inspection is performed. The number of generated particles or defects in each of the selected processes is estimated on the basis of the number of particles or defects in each of the selected processes and the distribution thereof. Then, the process in which the number of generated particles or defects is largest is picked out. The way of estimating the number of generated particles or defects is as follows. The distribution of particles or defects in one process is compared with the distribution of particles or defects in another process. If a result of the comparison shows that particles or defects are generated newly in a position where no particle or defect was generated in the first process, it is thought of that the particles or defects are generated in the second process. In this manner, the process in which particles or defects are generated frequently can be picked out (4003). Then, measures are taken against the cause of abnormality in line on the basis of the distribution of particles or defects on the wafer which has passed through the process (4004). If the process which becomes a problem is constituted by a plurality of apparatuses, an apparatus which becomes a problem can be identified by regarding the apparatuses as virtual processes in the steps 4003 and 4004.

As described above, according to the present invention, a coordinate system can be determined on the basis of one chip. Accordingly, the present invention can be smoothly adapted to characteristic dependent on the kind of each chip. Further, measures are taken speedily against abnormality in the production process by feeding results of estimation of the cause of semiconductor failure information back to a process in which the failure has occurred. Accordingly, wasteful production of defective semiconductors caused by time lag of detection of abnormality in the production process can be avoided as much as possible.

Further, in the present invention, measurement errors peculiar to observation apparatuses, analysis apparatuses and various inspection apparatuses used in this system can be corrected by calculating relative correction values even in the case where measurement errors are present between the respective apparatuses. Accordingly, failure analysis high in measurement accuracy can be performed speedily.

Further, in the present invention, the failure information is classified in relation to causes of failures and results of the classification are analyzed, so that even a person without specialized knowledge can perform failure analysis. Accordingly, even an unskilled operator can perform fail bit analysis easily and accurately.

What is claimed is:

1. A method for analyzing a failure on a semiconductor wafer, comprising:

displaying a distribution of fail bits on a wafer, having one or more chips, by using fail bit data acquired by a tester for each of memory cells included in the wafer and layout design information;

displaying a distribution of fail bits within a designated chip, based on (i) chip designation information, (ii) structural information within said chip and (iii) said fail bit data; and displaying distribution of fail bits in a part of the area of the overall distribution of fail bits within said chip on a memory cell basis, based on (iv) information for designating that area part, (v) said structural information within said chip and (vi) said fail bit data.

2. The method according to claim 1, wherein said displaying of the distribution of fail bits on the wafer further includes:

determining a shape of a representative fail bit distribution for each chip included in said wafer; and displaying the shape of the representative fail bit distribution for said each chip.

3. The method according to claim 2, wherein the number of occurrences of said shape of a representative fail bit distribution is additionally displayed for each of the chips.

4. The method according to claim 3, wherein the analysis of a failure is for a wafer constituted by an array of semiconductor chips.

5. The method according to claim 1, wherein said displaying of the distribution of fail bits within a designated chip further includes:

dividing said designated chip into a plurality of areas;

determining a shape of a representative fail bit distribution for each of the areas thus divided; and displaying the shape of the representative fail bit distribution for each of the areas thus divided.

6. The method according to claim 5, wherein the number of occurrences of said shape of a representative fail bit distribution is additionally displayed for each of the areas thus divided.

7. The method according to claim 6, wherein the analyzing of a failure is for a wafer constituted by an array of semiconductor chips.

8. The method according to claim 1, wherein the analyzing of a failure is for a wafer constituted by an array of semiconductor chips.

9. A system for analyzing a failure on a semiconductor wafer, comprising:

a storage unit for storing fail bit data acquired by a tester for each of memory cells included in said wafer, and layout design information;

a processing unit for (i) computing a distribution of fail bits on a wafer, having one or more chips, by using said fail bit data and said layout design information read from said storage unit, (ii) computing a distribution of fail bits within a chip designated by using chip designation information, structural information within said chip and said fail bit data, and (iii) computing a distribution of fail bits in a part of the area of the overall distribution of fail bits within said chip, on a memory cell basis, by using information for designating that area part, said structural information within said chip and said fail bit data; and a display unit for displaying said distribution of fail bits on the wafer, said distribution of fail bits within the chip, and said distribution of fail bits in said part of the area.

10. The system according to claim 9, wherein said processing unit determines a shape of representative fail bit distribution for each chip included in said wafer, and wherein said display unit displays the shape of the representative fail bit distribution for said each chip.

11. The system according to claim 10, wherein said display unit additionally displays the number of occurrences of said shape of a representative fail bit distribution for said each chip.

12. The system according to claim 11, wherein said semiconductor wafer is constituted by an array of semiconductor chips.

13. The system according to claim 9, wherein said processing unit divides said designated chip into a plurality of areas, and determines a shape of a representative fail bit distribution for each of the areas thus divided, and wherein said display unit displays the shape of the representative fail bit distribution for each of the areas thus divided.

14. The system according to claim 13, wherein said display unit additionally displays the number of occurrences of said shape of a representative fail bit distribution for each of the areas thus divided.

15. The system according to claim 14, wherein said semiconductor wafer is constituted by an array of semiconductor chips.

16. The system according to claim 9, wherein said semiconductor wafer is constituted by an array of semiconductor chips.

* * * * *